(12) United States Patent
Amidon et al.

(10) Patent No.: US 9,593,121 B2
(45) Date of Patent: Mar. 14, 2017

(54) INDOLE SUBSTITUTED PYRROLOPYRIMIDINYL INHIBITORS OF UBA6

(71) Applicant: Millennium Pharmaceuticals, Inc., Cambridge, MA (US)

(72) Inventors: Benjamin Stone Amidon, Arlington, MA (US); David P. Cardin, Wilmington (DE); Alexandra E. Gould, Cambridge, MA (US); Paul D. Greenspan, Acton, MA (US); Sean J. Harrison, Belmont, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/419,000

(22) PCT Filed: Aug. 2, 2013

(86) PCT No.: PCT/US2013/053358
§ 371 (c)(1),
(2) Date: Feb. 2, 2015

(87) PCT Pub. No.: WO2014/022744
PCT Pub. Date: Feb. 6, 2014

(65) Prior Publication Data
US 2015/0210700 A1 Jul. 30, 2015

Related U.S. Application Data

(60) Provisional application No. 61/679,109, filed on Aug. 3, 2012.

(51) Int. Cl.
| | | |
|---|---|---|
| *C07D 487/04* | (2006.01) | |
| *A61K 31/519* | (2006.01) | |
| *A61P 35/04* | (2006.01) | |
| *A61P 37/06* | (2006.01) | |
| *A61P 29/00* | (2006.01) | |

(52) U.S. Cl.
CPC ................... *C07D 487/04* (2013.01)

(58) Field of Classification Search
CPC ............................ C07D 487/04; A61K 31/519
See application file for complete search history.

(56) References Cited

U.S. PATENT DOCUMENTS

| | | |
|---|---|---|
| 7,951,810 B2 | 5/2011 | Critchley et al. |
| 8,008,307 B2 | 8/2011 | Claiborne et al. |
| 8,207,177 B2 | 6/2012 | Langston et al. |
| 8,481,550 B2 | 7/2013 | Claiborne et al. |
| 8,809,356 B2 | 8/2014 | McCarron et al. |
| 8,901,136 B2 | 12/2014 | Critchley et al. |
| 9,150,525 B2 | 10/2015 | Claiborne et al. |
| 9,290,500 B2 | 3/2016 | Afroze et al. |
| 2007/0191293 A1 | 8/2007 | Langston et al. |
| 2008/0051404 A1 | 2/2008 | Claiborne et al. |
| 2011/0021544 A1 | 1/2011 | Armitage et al. |
| 2012/0258927 A1 | 10/2012 | Langston et al. |
| 2013/0217682 A1 | 8/2013 | Afroze et al. |
| 2015/0011572 A1 | 1/2015 | McCarron et al. |
| 2016/0009744 A1 | 1/2016 | Duffey et al. |
| 2016/0039761 A1 | 2/2016 | Claiborne et al. |

FOREIGN PATENT DOCUMENTS

| | | |
|---|---|---|
| WO | WO 2007/092213 A2 | 8/2007 |
| WO | WO 2010/132110 A1 | 11/2010 |
| WO | WO 2015/002994 A2 | 1/2015 |

OTHER PUBLICATIONS

Ruschak, et al., (JNCI, 2011, vol. 103, (13), pp. 1007-1017).*
Eldridge, et al., (Cell Death and Differentiation, 2010, vol. 17, pp. 4-13).*
Brownell et al., "Substrate-Assisted Inhibition of Ubiquitin-Like Protein-Activating Enzymes: The NEDD8 E1 Inhibitor MLN4924 Forms a NEDD8-AMP Mimetic In Situ ," *Molecular Cell*, 37, pp. 102-111, (Jan. 15, 2010).
International Search Report and Written Opinion PCT/US2007/017463 dated Nov. 23, 2007 corresponding to U.S. Appl. No. 11/890,338.
Notice of Allowability dated Apr. 3, 2015, in U.S. Appl. No. 13/767,314.
Notice of Allowability dated Jul. 13, 2015, in U.S. Appl. No. 13/767,314.
Notice of Allowability dated Nov. 16, 2015, in U.S. Appl. No. 13/767,314.
PCT Notification of Transmittal of the International Search Report and the Written Opinion of the International Searching Authority, or the Declaration for International Application No. PCT/US2013/026113 mailed Apr. 11, 2013. (PCT corresponding to U.S. Appl. No. 13/767,314).
Restriction Requirement dated Dec. 19, 2014, in U.S. Appl. No. 13/767,314.
Supplementary European Search Report of European Application No. EP 13 74 8707, Jun. 9, 2015. (EP application corresponding to U.S. Appl. No. 13/767,314).
Pearce et al., "Failure modes in anticancer drug discovery and development," *Cancer Drug Design and Discovery*, Edited by Stephen Neidle, Chapter 18, pp. 424-435 (2008).
Gura, T., "Cancer Models: Systems for identifying new drugs are often faulty," *Science*, vol. 278, No. 5340. pp. 1041-1042, (Nov. 7, 1997).

(Continued)

*Primary Examiner* — Susanna Moore
(74) *Attorney, Agent, or Firm* — Millennium Pharmaceuticals, Inc

(57) ABSTRACT

Disclosed are chemical entities that inhibit Uba6, each of which is a compound of Formula (I) or a pharmaceutically acceptable salt thereof, wherein $R^{*1}$ is —H or —$CH_3$; and Y is Formula (II) or Formula (III), wherein $R^2$ is —H, —$CH_3$ or $C_{1-4}$ alkyloxycarbonyl; and $R^{S7.1}$, $R^{S7.2}$ and $R^{S8.1}$ are defined herein; pharmaceutical compositions comprising the chemical entities; and methods of using the chemical entities. These chemical entities are useful for treating disorders, particularly cell proliferation disorders, including cancers.

12 Claims, 1 Drawing Sheet

(56) References Cited

OTHER PUBLICATIONS

Johnson, JI et al., "Relationships between drug activity in NCI preclinical in vitro and in vivo models and early clinical trials," *British Journal of Cancer*, 64(10), pp. 1424-1431 (2001).
Simone, J.V., "Oncology: Introduction", *Cecil Textbook of Medicine, 20th Edition*, vol. 1, pp. 1004-1010, (1996).
Xu, G. Wei et al., "The ubiquitin-activating enzyme E1 as a therapeutic target for the treatment of leukemia and multiple myeloma," *Blood*, vol. 115, No. 11, pp. 2251-2259, (Mar. 18, 2010).
Liu L. et al., "As an independent prognostic factor, FAT10 promotes hepatitis B virus-related hepatocellular carcinoma progression via Akt/GSK3b pathway," *Oncogene*, 33, pp. 909-920, (2014).
Aichem, Annette et al., "USE1 is a bispecific conjugating enzyme for ubiquitin and FAT10, which FAT10ylates itself in cis," *Nature Communications*, 1:13, pp. 1-10, (May 4, 2010).
Canaan Allon et al., "FAT10/Diubiquitin-Like Protein-Deficient Mice Exhibit Minimal Phenotypic Differences," *Molecular and Cellular Biology*, pp. 5180-5189, (Jul. 2006).
Castellanos-Rubio, Ainara et al., "A regulatory single nucleotide polymorphism in the ubiquitin D gene associated with celiac disease," *Human Immunology*, 71, pp. 96-99, (2010).
Chiu, Yu-Hsin et al., "E1-L2 Activates Both Ubiquitin and FAT10," *Molecular Cell*, 27, pp. 1014-1023, (Sep. 21, 2007).
Supplementary European Search Report of European Application No. EP 13 825 181.4, Nov. 6, 2015.
Frank, Bernd et al., "Polymorphisms in inflammatory pathway genes and their association with colorectal cancer risk," *International Journal of Cancer*, 127, pp. 2822-2830, (2010).
International Preliminary Report on Patentability of PCT Application No. PCT/US2013/053358 filed on Aug. 2, 2013, and dated Feb. 3, 2015.
Jin, Jianping et al., "Dual E1 activation systems for ubiquitin diferentially regulate E2 enzyme charging," *Letters*, vol. 447, pp. 1135-1139, (Jun. 28, 2007).
Lee, Caroline GL et al., "Expression of the FAT10 gene is highly upregulated in hepatocellular carcinoma and other gastrointestinal and gynecological cancers," *Oncogene*, 22, pp. 2592-2603, (2003).
Lukasiak, S. et al., "Proinflammatory cytokines cause FAT10 upregulation in cancers of liver and colon," *Oncogene*, 27, pp. 6068-6074, (2008).
Merbi, Yifat et al., "Profiling of Ubipuitin-like Modifications Reveals Features of Mitotic Control," *Cell*, 152, pp. 1160-1172, (Feb. 28, 2013).
Zhang, DW et al., "p53 negatively regulates the expression of FAT10, a gene upregulatd in various cancers," *Oncogene*, 25, pp. 2318-2327, (2006).

* cited by examiner

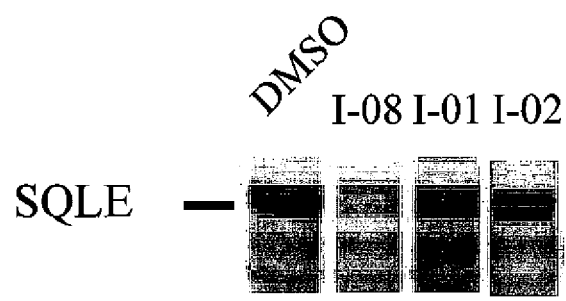

INDOLE SUBSTITUTED PYRROLOPYRIMIDINYL INHIBITORS OF UBA6

PRIORITY CLAIM

This application claims priority from U.S. Provisional Patent Application Ser. No. 61/679,109 filed on Aug. 3, 2012 which is hereby incorporated by reference in its entirety.

BACKGROUND

Ubiquitin is a small 76-amino acid protein that is the founding member of a family of posttranslational modifiers known as the ubiquitin-like proteins (Ubls). FAT10, originally identified as diubiquitin, is composed of two ubiquitin-like domains and is also a member of the Ubl family. W. Fan et al., *Immunogenetics*, 1996, 44(2), 97-103. Ubls play key roles in controlling many biological processes including cell division, cell signaling and the immune response. Ubls are small proteins that are covalently attached to a lysine on a target protein via an isopeptide linkage with a C-terminal glycine of the Ubl. The Ubl molecule alters the molecular surface of the target protein and can affect such properties as protein-protein interactions, enzymatic activity, stability and cellular localization of the target.

There are 8 known human Ubl activating enzymes (known as E1s). B. A. Schulman and J. W. Harper, *Nat Rev Mol Cell Biol*, 2009, 10, 319-31. Ubiquitin and other Ubls are activated by specific E1 enzymes which catalyze the formation of an acyl-adenylate intermediate with the C-terminal glycine of the Ubl. The activated Ubl molecule is then transferred to the catalytic cysteine residue within the E1 enzyme through formation of a thioester intermediate. The E1-Ubl intermediate and an E2 interact, resulting in a thioester exchange wherein the Ubl is transferred to the active site cysteine of the E2. The Ubl is then conjugated to the target protein, either directly or in conjunction with an E3 ligase, through isopeptide bond formation with the amino group of a lysine side chain in the target protein. Eukaryotic cells possess ~35 ubiquitin E2 enzymes and >500 ubiquitin E3 enzymes. The E3 enzymes are the specificity factors of the ubiquitin pathway which mediate the selective targeting of specific cellular substrate proteins. R. J. Deshaies and C. A. Joazeiro, *Annu Rev Biochem*, 2009, 78, 399-434; S. Lipkowitz and A. M. Weissman, *Nat Rev Cancer*, 2011, 11, 629-43; D. Rotin and S. Kumar, *Nat Rev Mol Cell Biol*, 2009, 10, 398-409.

Uba6 is a member of the E1 activating enzyme class of enzymes and was identified in 2007 as an alternate ubiquitin activating enzyme. J. Jin et al., *Nature*, 2007, 447(7148), 1135-38; Y. H. Chiu et al., *Mol Cell*, 2007, 27(6), 1014-23; C. Pelzer et al., *J Biol Chem*, 2007, 282(32), 23010-14. Uba6 has been shown to play a role in cytoplasmic N-end rule ubiquitin-mediated protein degradation. P. C. Lee et al., *Mol Cell*, 2011, 43(3), 392-405. The mouse knockout of Uba6 has an early embryonic lethal phenotype which supports an essential role for this enzyme. In addition tissue specific knockouts of Uba6 have unique phenotypes. Mice with Uba6 knocked out in all tissue originating from the neural crest have altered neuronal development. P. Lee, et al., *Mol Cell*, 2013, 50(2), 172-84. Uba6 also activates a Ubiquitin-like protein (Ubl) called FAT10 (or UBD). Y. H. Chiu et al., *Mol Cell*, 2007, 27(6), 1014-23. While this Ubl is dispensable for mouse development, the loss of FAT10 systemically is associated with a dramatic increase in sensitivity to bacterial challenge. A. Canaan, et al., *Mol Cell Biol*, 2006, 13:5180-89. Moreover, accumulation of FAT10 has been noted in hepatic and colon cancer as well as inflammatory bowel disease, Celiac disease and Crohn's disease. C. G. Lee, et al., *Oncogene*, 2003, 22(17), 2592-603; S. Lukasiak et al., *Oncogene*, 2008, 27(46), 6068-74. FAT10 expression has been shown to be negatively affected by the known tumor suppressor p53 (D. Zhang et al., *Oncogene*, 2006, 25(16), 2318-27) and in turn FAT10 conjugation has been shown to affect p53 function (T. Li, et al., *Arch Biochem Biophys* 2011, 509(2), 164-9). It has also been reported that FAT10 plays a role in mitotic progression, however this may only occur in certain cell types or conditions such as inflammation. Y. Merbl, *Cell*, 2013, 152, 1160-72. There is a Uba6-specific E2 enzyme (Use1) that has been identified to productively interact only with Uba6, but not Uba1. J. Jin et al., *Nature*, 2007, 447(7148), 1135-38. Use1 can accept activated ubiquitin or FAT10. A. Aichem et al., *Nat Commun*, 2010, 1, 13.

Although the role of Uba6 in ubiquitin metabolism may be modest relative to the better characterized Uba1, the knock out data confirms that Uba6 must play an essential role in cell proliferation. The essential function of Uba6 may not be confined to its activation of either ubiquitin or FAT10, but potentially a combination of the two, therefore representing a possible synthetic lethal interaction with the potential for anti-cancer effects. Accordingly, small molecule inhibitors of Uba6 would be expected to act as potent anti-proliferative agents such as in tumors that overexpress FAT10 (gastrointestinal, gynecological and hepatic origin), and may have utility as a general oncology chemotherapeutic L. Liu, Oncogene, 2013 advanced online publication Jul. 1, 2013. The inhibition of Uba6 function should also impact FAT10 metabolism. A small molecule inhibitor of Uba6 would therefore also be expected to have use in the anti-inflammatory and immunologic setting, such as in the treatment of inflammatory bowel disease, Crohn's disease (B. Frank et al., *Int J Cancer*, 2010, 927(12), 2822-30) and Celiac disease (A. Castellanos-Rubio et al., *Hum Immunol*, 2010, 79(1), 96-99).

FIGURES

FIG. 1 shows a Western blot depicting the effect of compounds on SREBP-dependent lipid metabolism.

SUMMARY

In one aspect, the invention relates to chemical entities, each of which is a compound of Formula I:

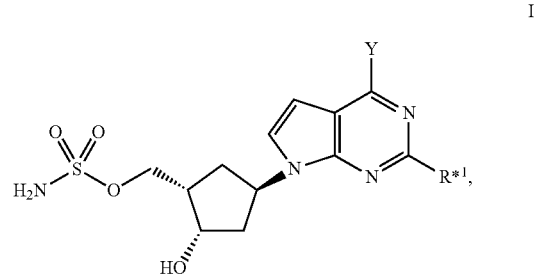

or a pharmaceutically acceptable salt thereof, wherein $R^{*1}$ is —H or —CH$_3$; and Y is

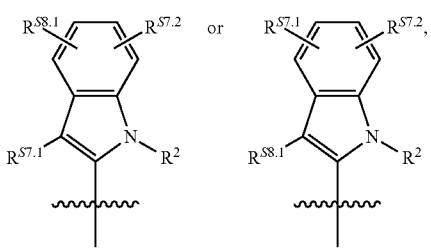

wherein R² is —H, —CH₃ or $C_{1-4}$ alkyloxycarbonyl; and $R^{S7.1}$, $R^{S7.2}$ and $R^{S8.1}$ are defined below.

In one aspect, the invention relates to compositions comprising one or more of the chemical entities and one or more pharmaceutically acceptable carriers.

In one aspect, the invention relates to methods of treating cancer comprising administering to a patient in need of such treatment one or more of the chemical entities.

DESCRIPTION

Definitions

Unless otherwise specified, as used herein, alone or as part of another group, "halo" or "halogen" refers to fluoro, chloro, bromo or iodo.

Unless otherwise specified, as used herein, alone or as part of another group, "alkyl" refers to a straight-chain or branched saturated hydrocarbyl group having from 1 to 8 carbon atoms. In some embodiments, an alkyl group can have from 1 to 6 carbon atoms. In some embodiments, an alkyl group can have from 1 to 4 carbon atoms. In some embodiments, an alkyl group can have from 1 to 3 carbon atoms. Examples of $C_{1-3}$ alkyl groups include methyl, ethyl, propyl and isopropyl. Examples of $C_{1-4}$ alkyl groups include the aforementioned $C_{1-3}$ alkyl groups as well as butyl, isobutyl, sec-butyl and Pert-butyl. Examples of $C_{1-6}$ alkyl groups include the aforementioned $C_{1-4}$ alkyl groups as well as pentyl, isopentyl, neopentyl, hexyl and the like. Additional examples of alkyl groups include heptyl, octyl and the like.

Unless otherwise specified, as used herein, alone or as part of another group, "alkenyl" refers to a straight-chain or branched hydrocarbyl group having from 2 to 8 carbon atoms and one or more carbon-carbon double bonds. In some embodiments, an alkenyl group can have from 2 to 6 carbon atoms. In some embodiments, an alkenyl group can have from 2 to 4 carbon atoms. The one or more carbon-carbon double bonds can be internal (such as in 2-butenyl) or terminal (such as in 1-butenyl). Examples of $C_{2-4}$ alkenyl groups include ethenyl, 1-propenyl, 2-propenyl, 1-butenyl, 2-butenyl, butadienyl and the like. Examples of $C_{2-6}$ alkenyl groups include the aforementioned $C_{2-4}$ alkenyl groups as well as pentenyl, pentadienyl, hexenyl and the like. Additional examples of alkenyl include heptenyl, octenyl, octatrienyl and the like.

Unless otherwise specified, as used herein, alone or as part of another group, "alkynyl" refers to a straight-chain or branched hydrocarbyl group having from 2 to 8 carbon atoms and one or more carbon-carbon triple bonds. In some embodiments, an alkynyl group can have from 2 to 6 carbon atoms. In some embodiments, an alkynyl group can have from 2 to 4 carbon atoms. The one or more carbon-carbon triple bonds can be internal (such as in 2-butynyl) or terminal (such as in 1-butynyl). Examples of $C_{2-4}$ alkynyl groups include ethynyl, propyn-1-yl, propyn-3-yl, 1-butyn-1-yl, 1-butyn-4-yl, 2-butyn-1-yl and the like. Examples of $C_{2-6}$ alkynyl groups include the aforementioned $C_{2-4}$ alkynyl groups as well as pentynyl, hexynyl and the like. Additional examples of alkynyl include heptynyl, octynyl and the like.

Unless otherwise specified, as used herein, alone or as part of another group, "aliphatic" refers to alkyl, alkenyl and alkynyl groups as defined above. For example, if a moiety can be substituted with "$C_{1-6}$ aliphatic", it can be substituted with $C_{1-6}$ alkyl, $C_{2-6}$ alkenyl or $C_{2-6}$ alkynyl.

Unless otherwise specified, each instance of "optionally substituted" alkyl, alkenyl or alkynyl (collectively, "optionally substituted" aliphatic) is independently unsubstituted or substituted with 1-3, 1-2 or 1 substituent(s):

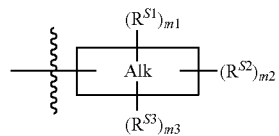

wherein

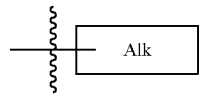

represents the alkyl, alkenyl or alkynyl group, respectively, and each of m1+m2 and m3 is independently 0 (i.e., $R^{S[1,2,3]}$ is —H) or 1.

In some embodiments, m1+m2+m3≤2. In some embodiments, m1+m2+m3≤1.

Unless otherwise specified, as used herein, alone or as part of another group, "alkylene" refers to a diradical of a straight-chain or branched saturated hydrocarbon group having from 1 to 6 carbon atoms. In some embodiments, an alkylene group can have from 1 to 4 carbon atoms. In some embodiments, an alkylene group can have from 1 to 2 carbon atoms. Examples of $C_{1-2}$ alkylene groups include methylene and ethylene. Examples of $C_{1-4}$ alkylene groups include the aforementioned $C_{1-2}$ alkylene groups as well as trimethylene (1,3-propanediyl), propylene (1,2-propanediyl), tetramethylene (1,4-butanediyl), butylene (1,2-butanediyl), 1,3-butanediyl, 2-methyl-1,3-propanediyl and the like. Examples of $C_{1-6}$ alkylene groups include the aforementioned $C_{1-4}$ alkylene groups as well as pentamethylene (1,5-pentanediyl), pentylene (1,2-pentanediyl), hexamethylene (1,6-hexanediyl), hexylene (1,2-hexanediyl), 2,3-dimethyl-1,4-butanediyl and the like. In some embodiments ("α,ω-alkylene"), an alkylene group is an α,ω-diradical. Examples of α,ω-alkylene groups include methylene, ethylene, trimethylene, tetramethylene, pentamethylene and hexamethylene.

Unless otherwise specified, as used herein, alone or as part of another group, "alkenylene" refers to a diradical of a straight-chain or branched hydrocarbon group having from 2 to 6 carbon atoms and one or more carbon-carbon double bonds. In some embodiments, an alkenylene group can have from 2 to 4 carbon atoms. In some embodiments, an alkenylene group can have 2 carbon atoms, i.e., ethenediyl. The one or more carbon-carbon double bonds can be internal (such as in 1,4-but-2-enediyl) or terminal (such as in 1,4- but-1-enediyl). Examples of $C_{2-4}$ alkenylene groups include ethenediyl, 1,2-propenediyl, 1,3-propenediyl, 1,4-but-1-enediyl, 1,4-but-2-enediyl and the like. Examples of $C_{2-6}$ alkenylene groups include the aforementioned $C_{2-4}$ alkenylene groups as well as 1,5-pent-1-enediyl, 1,4-pent-2-enediyl, 1,6-hex-2-enediyl, 2,5-hex-3-enediyl, 2-methyl-1,4-pent-2-enediyi and the like. In some embodiments ("α,ω-alkenylene"), an alkenylene group is an α,ω-diradical. Examples of α,ω-alkenylene groups include ethenediyl, 1,3-propenediyl, 1,4-but-2-enediyl, 1,5-pent-1-enediyl, 1,6-hex-3-enediyl and the like.

Unless otherwise specified, as used herein, alone or as part of another group, "alkynylene" refers to a diradical of a straight-chain or branched hydrocarbon group having from 2 to 6 carbon atoms and one or more carbon-carbon triple bonds. In some embodiments, an alkynylene group can have from 2 to 4 carbon atoms. In some embodiments, an alkynylene group can have 2 carbon atoms, i.e., ethynediyl. The one or more carbon-carbon triple bonds can be internal (such as in 1,4-but-2-ynediyl) or terminal (such as in 1,4-but-1-ynediyl). Examples of $C_{2-4}$ alkynylene groups include ethynediyl, 1,3-propynediyl, 1,4-but-1-ynediyl, 1,4-but-2-ynediyl and the like. Examples of $C_{2-6}$ alkynylene groups include the aforementioned $C_{2-4}$ alkynylene groups as well as 1,5-pent-1-ynediyl, 1,4-pent-2-ynediyl, 1,6-hex-2-ynediyi, 2,5-hex-3-ynediyl, 3-methyl-1,5-hex-1-ynediyl and the like. In some embodiments ("α,ω-alkynylene"), an alkynylene group is an α,ω-diradical. Examples of α,ω-alkynylene groups include ethynediyl, 1,3-propynediyl, 1,4-but-2-ynediyl, 1,5-pent-1-ynediyl, 1,6-hex-3-ynediyl and the like.

Unless otherwise specified, as used herein, alone or as part of another group, "hateroalkylene" refers to a diradical having the structure $C_{n1}$ alkylene[ψ]$C_{n2}$ alkylene, wherein n1 and n2 are whole numbers, at least one of which is other than zero ($C_0$ alkylene is a covalent bond), and ψ is —O—, —NH—, —N(CH$_3$)— or —S—. $C_{0-3,0-3}$ heteroalkylene refers to $C_{n1}$ alkylene[ψ]$C_{n2}$ alkylene, wherein each of n1 and n2 is independently 0, 1, 2 or 3, provided that n1+n2 is 1, 2, 3 or 4. $C_{0-2,0-2}$ heteroalkylene refers to $C_{n1}$ alkylene [ψ]$C_{n2}$ alkylene, wherein each of n1 and n2 is independently 0, 1 or 2, provided that n1+n2 is 1, 2, 3 or 4. Examples of heteroalkylene groups include —OCH$_2$—, —NHCH$_2$CH$_2$—, SCH$_2$CH$_2$CH$_2$, —OCH(CH$_3$)CH$_2$—, —CH$_2$N(CH$_3$)—, —CH$_2$OCH$_2$—, —CH$_2$NHCH$_2$CH$_2$—, —CH$_2$SCH$_2$CH$_2$—, CH$_2$OCH(CH$_3$)CH$_2$—, —CH$_2$CH$_2$NH—, —CH$_2$CH$_2$N(CH$_3$)CH$_2$—, —CH$_2$CH$_2$OCH$_2$CH$_2$—, —CH(CH$_3$)CH$_2$S—, CH(CH$_3$)CH$_2$OCH$_2$— and the like.

Unless otherwise specified, as used herein, alone or as part of another group, "haloalkyl" refers to an alkyl group, wherein one or more of the hydrogen atoms are each independently replaced with halo. In some embodiments ("perhaloalkyl"), all of the hydrogen atoms are each replaced with fluoro or chloro. In some embodiments ("perfluoroalkyl"), all of the hydrogen atoms are each replaced with fluoro. Examples of perfluoroalkyl groups include —CF$_3$, —CF$_2$CF$_3$, —CF$_2$CF$_2$CF$_3$ and the like. Examples of perhaloalkyl groups include the aforementioned perfluoroalkyl groups as well as —CCl$_3$, —CFCl$_2$, —CF$_2$Cl, —CCl$_2$CCl$_3$ and the like. Examples of haloalkyl groups include the aforementioned perhaloalkyl groups as well as —CH$_2$F, —CHF$_2$, —CH$_2$Cl, —CH$_2$Br, —CH(Cl)CH$_2$Br, —CH$_2$CH(F)CH$_2$Cl and the like.

Unless otherwise specified, as used herein, alone or as part of another group, "alkoxy" or "alkyloxy" refers to an —O-alkyl group having from 1 to 8 carbon atoms. In some embodiments, an alkoxy group can have from 1 to 6 carbon atoms. In some embodiments, an alkoxy group can have from 1 to 4 carbon atoms. Examples of $C_1$-4 alkoxy groups include methoxy, ethoxy, propoxy, isopropoxy, butoxy, tert-butoxy and the like. Examples of $C_{1-6}$ alkoxy groups include the aforementioned $C_{1-4}$ alkoxy groups as well as pentyloxy, isopentyloxy, neopentyloxy, hexyloxy and the like. Additional examples of alkoxy groups include heptyloxy, octyloxy and the like.

Unless otherwise specified, as used herein, alone or as part of another group, "haloalkoxy" refers to an alkoxy group, wherein one or more of the hydrogen atoms are each independently replaced with halo. In some embodiments ("perhaloalkoxy"), all of the hydrogen atoms are each replaced with fluoro or chloro. In some embodiments ("perfluoroalkoxy"), all of the hydrogen atoms are each replaced with fluoro. Examples of perfluoroalkoxy groups include —OCF$_3$, —OCF$_2$CF$_3$, —OCF$_2$CF$_2$CF$_3$ and the like. Examples of perhaloalkoxy groups include the aforementioned perfluoroalkoxy groups as well as —OCCl$_3$, —OCFCl$_2$, —OCF$_2$Cl, —OCCl$_2$CCl$_3$ and the like. Examples of haloalkoxy groups include the aforementioned perhaloalkoxy groups as well as —OCH$_2$F, —OCHF$_2$, —OCH$_2$Cl, —OCH$_2$Br, —OCH(Cl)CH$_2$Br, —OCH$_2$CH(F) CH$_2$Cl and the like.

Unless otherwise specified, as used herein, alone or as part of another group, "alkylthio" refers to an —S-alkyl group having from 1 to 8 carbon atoms. In some embodiments, an alkylthio group can have from 1 to 6 carbon atoms. In some embodiments, an alkylthio group can have from 1 to 4 carbon atoms. Examples of $C_{1-4}$ alkylthio groups include methylthio, ethylthio, propylthio, isopropylthio, butylthio, isobutylthio and the like. Examples of $C_{1-6}$ alkylthio groups include the aforementioned $C_{1-4}$ alkylthio groups as well as pentylthio, isopentylthio, hexylthio and the like. Additional examples of alkylthio groups include heptylthio, octylthio and the like.

Unless otherwise specified, as used herein, alone or as part of another group, "haloalkylthio" refers to an alkylthio group, wherein one or more of the hydrogen atoms are each independently replaced with halo. In some embodiments ("perhaloalkylthio"), all of the hydrogen atoms are each replaced with fluoro or chloro. In some embodiments ("perfluoroalkylthio"), all of the hydrogen atoms are each replaced with fluoro. Examples of perfluoroalkylthio groups include —SCF$_3$, —SCF$_2$CF$_3$, —SCF$_2$CF$_2$CF$_3$ and the like. Examples of perhaloalkylthio groups include the aforementioned perfluoroalkylthio groups as well as —SCCl$_3$, —SCFC$_2$, —SCF$_2$Cl, —SCCl$_2$CCl$_3$ and the like. Examples of haloalkylthio groups include the aforementioned perhaloalkylthio groups as well as —SCH$_2$F, —SCHF$_2$, —SCH$_2$Cl, —SCH$_2$Br, —SCH(Cl)CH$_2$Br, —SCH$_2$CH(F) CH$_2$Cl and the like.

Illustrative examples of aryl, carbocyclyl, heteroaryl, heterocyclyl, fused aryl, fused carbocyclyl, fused heteroaryl and fused heterocyclyl are shown in the table below, in which X represents a heteroatom such as N, O or S. These examples are intended merely to illustrate the differences between the radicals and are not in any way intended to limit any other feature shown, e.g., position of attachment (except in the fused rings, where the point of attachment must be on the ring type shown), position of the heteroatom(s), number of heteroatoms, size of rings, number of rings, etc.

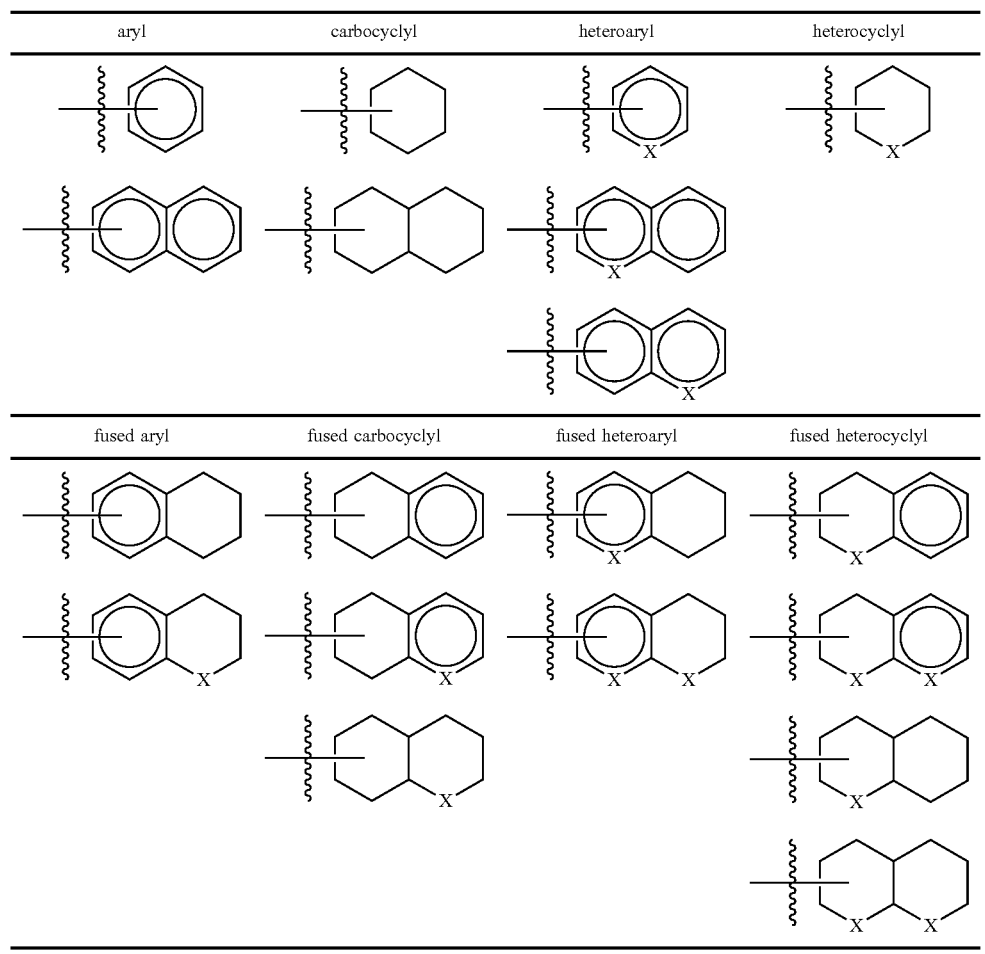

Unless otherwise specified, as used herein, alone or as part of another group, "aryl" refers to a radical of an aromatic monocyclic or bicyclic ring system having from 6 to 10 ring carbon atoms. Examples of such aryl groups include phenyl, 1-naphthyl and 2-naphthyl and the like.

Unless otherwise specified, each instance of an "optionally substituted" aryl group is independently unsubstituted or substituted with 1-4, 1-3, 1-2 or 1 substituent(s):

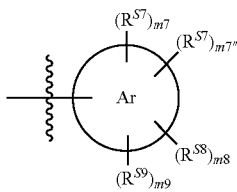

wherein

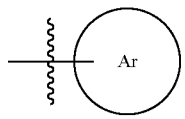

represents the aryl group
and each of m7, m7", m8 and m9 is independently 0 (i.e., $R^{S[7,8,9]}$ is —H) or 1.

In some embodiments, m7+m7"+m8+m9≤3. In some embodiments, m7+m7"+m8+m9≤2. In some embodiments, m7+m7"+m8+m9≤1.

Unless otherwise specified, as used herein, alone or as part of another group, "carbocyclyl" refers to a radical of a non-aromatic cyclic hydrocarbon group having from 3 to 10 ring carbon atoms. In some embodiments ("$C_{3-8}$ carbocyclyl"), a carbocyclyl group has from 3 to 8 ring carbon atoms. In some embodiments ("$C_{3-6}$ carbocyclyl"), a carbocyclyl group has from 3 to 6 ring carbon atoms. Examples of $C_{3-6}$ carbocyclyl groups include cyclopropyl, cyclobutyl, cyclopentyl, cyclopentenyl, cyclohexyl, cyclohexenyl, cyclohexadienyl and the like. Examples of Cm carbocyclyl groups include the aforementioned $C_{3-6}$ carbocyclyl groups as well as cycloheptyl, cycloheptadienyl, cycloheptatrienyl, cyclooctyl, bicyclo[2.2.1]heptanyl, bicyclo[2.2.2]octanyl and the like. Examples of $C_{3-10}$ carbocyclyl groups include the aforementioned $C_{3-8}$ carbocyclyl groups as well as octahydro-1H-indenyl, decahydronaphthalenyl, spiro[4.5] decanyl and the like. As the foregoing examples illustrate, a carbocyclyl group can be monocyclic or bicyclic (e.g., containing a fused, bridged or spiro ring system), and can be saturated or can contain one or more carbon-carbon double or triple bonds.

In some embodiments ("cycloalkyl"), a carbocyclyl group is monocyclic, saturated, and has 3 to 8 ring carbon atoms. In some embodiments ("$C_3$-6 cycloalkyl"), a cycloalkyl group has 3 to 6 ring carbon atoms. In some embodiments ("$C_{5-6}$ cycloalkyl"), a cycloalkyl group has 5 or 6 ring carbon atoms. Examples of $C_{5-6}$ cycloalkyl groups include cyclopentyl and cyclohexyl. Examples of $C_{3-6}$ cycloalkyl groups include the aforementioned $C_{5-6}$ cycloalkyl groups as well as cyclopropyl and cyclobutyl. Examples of $C_{3-8}$ cycloalkyl groups include the aforementioned $C_{3-6}$ cycloalkyl groups as well as cycloheptyl and cyclooctyl.

Unless otherwise specified, each instance of an "optionally substituted" carbocyclyl group is independently unsubstituted or substituted with 1-3, 1-2 or 1 substituent(s):

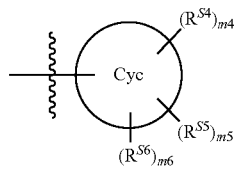

wherein

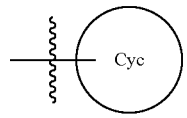

represents the carbocyclyl group, and each of m4, m5 and m6 is independently 0 (i.e., $R^{S[4,5,6]}$ is —H) or 1.

In some embodiments, m4+m5+m6≤2. In some embodiments, m4+m5+m6≤1.

Unless otherwise specified, as used herein, atone or as part of another group, "heteroaryl" refers to a radical of a 5- to 10-membered aromatic ring system having ring carbon atoms and 1 to 4 ring heteroatoms, each heteroatom independently selected from N, O and S. Examples of such heteroaryl groups include pyrrolyl, furanyl (furyl), thiophenyl (thienyl), pyrazolyl, imidazolyl, oxazolyl, isoxazolyl, thiazolyl, triazolyl, oxadiazolyl, thiadiazolyl, tetrazolyl, pyridinyl (pyridyl), pyridazinyl, pyrimdinyl, pyrazinyl, triazinyl, indolyl, benzofuranyl, benzothiophenyl (benzothienyl), indazolyl, benzimidazolyl, benzoxazolyl, benzisoxazolyl, benzothiazolyl, quinolinyl, isoquinolinyl, cinnolinyl, quinazolinyl, quinoxalinyl, phthalazinyl, naphthyridinyl and the like.

As the foregoing examples illustrate, a heteroaryl group can be monocyclic or bicyclic. In some embodiments the heteroaryl group is monocyclic and has 5 to 6 ring atoms. In some embodiments the heteroaryl group is monocyclic and has 5 to 6 ring atoms, 1 or 2 of which are heteroatoms. In some embodiments the heteroaryl group is bicyclic and has 8 to 10 ring atoms. In some embodiments the heteroaryl group is bicyclic and has 9 to 10 ring atoms, 1-3 of which are heteroatoms. In some embodiments the heteroaryl group is bicyclic and has 9 to 10 ring atoms, 1 or 2 of which are heteroatoms.

Unless otherwise specified, each instance of an "optionally substituted" heteroaryl group is independently unsubstituted or substituted with 1-4, 1-3, 1-2 or 1 substituent(s):

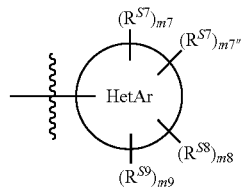

wherein

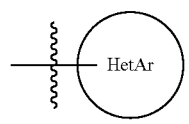

represents the heteroaryl group, and each of m7, m7", m8 and m9 is independently 0 (i.e., $R^{S[7,8,9]}$ is —H) or 1.

In some embodiments, m7+m7"+m8+m9≤3. In some embodiments, m7+m7"+m8+m9≤2. In some embodiments, m7+m7"+m8+m9≤1.

Unless otherwise specified, as used herein, alone or as part of another group, "heterocyclyl" refers to a radical of a monocyclic 3- to 7-membered non-aromatic ring system having ring carbon atoms and 1 to 3 ring heteroatoms, each heteroatom independently selected from N, O and S, wherein each ring carbon atom that is bonded to a ring heteroatom can also be bonded to an oxo (═O) group (such that the ring carbon atom is the carbon atom of a carbonyl (—C(═O)— group). Examples of heterocyclyl groups include oxiranyl, aziridinyl, oxetanyl, azetidinyl, pyrrolidinyl, dihydropyrrolyl, tetrahydrofuranyl, dihydrofuranyl, tetrahydrothiophenyl, dihydrothiophenyl, pyrazolidinyl, imidazolidinyl, oxazolidinyl, isoxazolidinyl, thiazolidinyl, triazolidinyl, oxadiazolidinyl, piperidinyl, tetrahydropyridinyl, dihydropyridinyl, piperazinyl, tetrahydropyranyl, dioxanyl, morpholinyl, triazinanyl, azepanyl, diazepanyl, diazepinyl, oxepanyl, dioxepanyl, oxazepanyl, oxazepinyl and the like. In some embodiments, the heterocyclyl group has 1 or 2 ring heteroatoms. In some embodiments, the heterocyclyl group has from 5 to 6 ring atoms, 1 or 2 of which are heteroatoms.

Unless otherwise specified, each instance of an "optionally substituted" heterocyclyl group is independently unsubstituted or substituted with 1-3, 1-2 or 1 substituent(s):

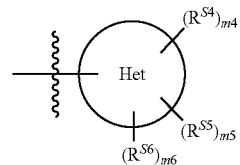

wherein

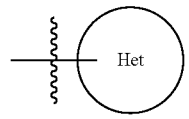

represents the heterocyclyl group,
and each of m4, m5 and m6 is independently 0 (i.e., $R^{S[4,5,6]}$ is —H) or 1.

In some embodiments, m4+m5+m6≤2. In some embodiments, m4+m5+m6≤1.

Unless otherwise specified, as used herein, alone or as part of another group, "fused aryl" refers to an aryl group in which two adjacent ring atoms, together with additional atoms, form a carbocycle or heterocycle (as defined with reference to "carbocyclyl" and "heterocyclyl", respectively). Examples of fused aryl groups include 1,2,3,4-tetrahydronaphthalen-5-yl, 1,2,3,4-tetrahydronaphthalen-6-yl, 2,3-dihydro-1H-inden-4-yl, 2,3-dihydro-1H-inden-5-yl, 1H-inden-4-yl, 2,2-dimethyl-2,3-dihydrobenzofuran-7-yl, 1,1-dimethyl-1,3-dihydroisobenzofuran-4-yl, benzo[d][1,3]dioxol-4-yl, 1,2,3,4-tetrahydroquinoxalin-5-yl, 2,2-dimethyl-3,4-dihydro-2H-benzo[b][1,4]oxazin-6-yl and the like.

Unless otherwise specified, each instance of an "optionally substituted" fused aryl group is independently unsubstituted or substituted with 1-4, 1-3, 1-2 or 1 substituent(s):

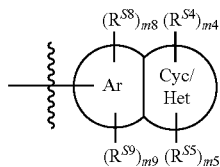

wherein

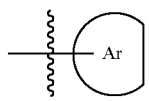

represents the aryl group,
and

represents the carbocycle or heterocycle,
and each of m4, m5, m8 and m9 is independently 0 (i.e., $R^{S[4,5,8,9]}$ is —H) or 1.

In some embodiments, m4+m5+m8+m9≤3. In some embodiments, m4+m5+m8+m9≤2. In some embodiments, m4+m5+m8+m9≤1.

Unless otherwise specified, as used herein, alone or as part of another group, "fused carbocyclyl" refers to a carbocyclyl group in which two adjacent ring atoms, together with additional atoms, form an aromatic or heteroaromatic ring (as defined with reference to "aryl" and "heteroaryl", respectively), or in which two ring atoms, together with additional atoms, form a heterocycle (as defined with reference to "heterocyclyl"). Examples of fused carbocyclyl groups include 1,2,3,4-tetrahydronaphthalen-1-yl, 1,2,3,4-tetrahydronaphthalen-2-yl, 2,3-dihydro-1H-inden-1-yl, 2,3-dihydro-1H-inden-2-yl, 1H-inden-1-yl, 5,6,7,8-tetrahydroquinolin-5-yl, 5,6,7,8-tetrahydroquinolin-7-yl, 4,5,6,7-tetrahydro-1H-indol-4-yl, 4,5,6,7-tetrahydro-1H-indol-6-yl, 4,5,6,7-tetrahydrobenzofuran-7-yl and the like.

Unless otherwise specified, as used herein, alone or as part of another group, "fused heteroaryl" refers to a heteroaryl group in which two adjacent ring atoms, together with additional atoms, form a carbocycle or heterocycle (as defined with reference to "carbocyclyl" and "heterocyclyl", respectively). Examples of fused heteroaryl groups include 4,5,6,7-tetrahydro-1H-indol-2-yl, 4,5,6,7-tetrahydro-1H-indol-3-yl, 4,5,6,7-tetrahydrobenzofuran-2-yl, 4,5,6,7-tetrahydrobenzofuran-3-yl, 4,5,6,7-tetrahydrobenzothiophen-2-yl, 4,5,6,7-tetrahydrobenzothiophen-3-yl, 4,5,6,7-tetrahydro-1H-pyrrolo[2,3-b]pyridin-2-yl, 4,5,6,7-tetrahydro-1H-pyrrolo[2,3-b]pyridin-3-yl, 1,4,5,7-tetrahydropyrano[3,4-b]pyrrol-2-yl, 1,4,5,7-tetrahydropyrano[3,4-b]pyrrol-3-yl, 4,5,6,7-tetrahydrofuro[3,2-c]pyridin-2-yl, 4,5,6,7-tetrahydrofuro[3,2-c]pyridin-3-yl, 6,7-dihydro-5H-furo[3,2-b]pyran-2-yl, 6,7-dihydro-5H-furo[3,2-b]pyran-3-yl, 4,5,6,7-tetrahydrothieno[3,2-b]pyridin-2-yl, 4,5,6,7-tetrahydrothieno[3,2-b]pyridin-3-yl, 5,7-dihydro-4H-thieno[2,3-c]pyran-2-yl, 5,7-dihydro-4H-thieno[2,3-c]pyran-3-yl and the like.

Unless otherwise specified, as used herein, alone or as part of another group, "fused heterocyclyl" refers to a heterocyclyl group in which two adjacent ring atoms, together with additional atoms, form an aromatic or heteroaromatic ring (as defined with reference to "aryl" and "heteroaryl", respectively), or in which two ring atoms, together with additional atoms, form a carbocycle or heterocycle (as defined with reference to "carbocyclyl" and "heterocyclyl", respectively). Examples of fused heterocyclyl groups include indolin-1-yl, indolin-2-yl, indolin-3-yl, tetrahydroisoindol-1-yl, tetrahydroisoindol-2-yl, dihydrobenzofuran-2-yl, dihydrobenzofuran-3-yl, dihydrobenzothien-2-yl, dihydrobenzothien-3-yl, 1,2,3,4-tetrahydroquinolin-1-yl, 1,2,3,4-tetrahydroquinolin-2-yl, 1,2,3,4-tetrahydroquinolin-3-yl, 1,2,3,4-tetrahydroquinolin-4-yl, chroman-2-yl, chroman-3-yl, chroman-4-yl, chromen-2-yl, chromen-3-yl, chromen-4-yl, thiochroman-3-yl, isochroman-4-yl, 1H-benzo[e][1,4]diazepin-2-yl, 2,3-dihydro-1H-pyrrolo[2,3-b]pyridin-1-yl, 2,3-dihydro-1H-pyrrolo[2,3-b]pyridin-2-yl, 2,3-dihydro-1H-pyrrolo[2,3-b]pyridin-3-yl, 2,3-dihydrofuro[2,3-b]pyridin-3-yl, 5,6-dihydro-4H-furo[3,2-b]pyrrol-6-yl, 1,2,3,4-tetrahydro-1,6-naphthyridin-3-yl, decahydroquinolinyl, decahydroisoquinolinyl, octahydrochromenyl, octahydroisochromenyl, decahydronaphthyridinyl, 2-azabicyclo[2.2.2]octan-2-yl, 2-azabicyclo[2.2.2]octan-3-yl, 2,5-diazabicyclo[2.2.2]octan-2-yl, 2,5-diazabicyclo[2.2.2]octan-6-yl, 3,3-dimethyl-1,3-dihydroisobenzofuran-1-yl, 2,3-dihydrobenzofuran-3-yl, 6-((trifluoromethyl)thio)-2,3-dihydrobenzofuran-3-yl, 2,3-dihydronaphtho[1,2-b]furan-3-yl, 2,3,4,5-tetrahydrobenzo[b]oxepin-5-yl and the like.

Unless Otherwise Specified— each instance of $R^{S1}$ is independently selected from —H, (a) halo, (c) —OR*², (d) —N(R*²)₂ and (e) —SRt†2;

each instance of $R^{S2}$ is independently selected from —H, (a) halo, (c) —OR*⁴, (d) —N(R*⁴)₂, (e) —SR†⁴, (h) —NO₂, (i) —CN, (j) —C(O)—R†⁴, (k) —C(O)—OR*⁴, (l) —C(O)—N(R*⁴)₂, (m) —O—C(O)—R†⁴ (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;

each instance of $R^{S3}$ is independently selected from (a) halo, (c) —OR*⁴, (d) —N(R*⁴)₂, (e) —SR†⁴, (h) —NO₂, (i) —CN, (j) —C(O)—R†⁴, (k) —C(O)—OR*⁴, (l) —C(O)—N(R*⁴)₂, (m) —O—C(O)—R⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴, (r) —N(R*⁴)—C(O)—N(R*⁴)₂, (aa) $C_{3-6}$ carbocyclyl, (cc) 5- to 6-membered heterocyclyl, (ee) $C_6$ aryl and (gg) 5- to 6-membered heteroaryl; wherein each of (aa) and (cc) is optionally substituted with 1-3 groups independently selected from (a) halo, (b1) $C_{1-2}$ aliphatic, (b2) $R^{\#2-1}$ (c) —OR*², (d) —N(R*²)₂ and (e) —SR†²; and wherein each of (ee) and (gg) is optionally substituted with 1-3 groups independently selected from (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S4}$ is independently selected from —H, (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S4}$ is independently selected from —H, (a) halo, (b1) $C_{1-4}$ aliphatic, (b2) $R^{\#4-2}$, (c) —OR*⁴, (d) —N(R*⁴)₂, (e) —SR†⁴, (f) $C_{1-3}$ haloalkyl, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂;

each instance of $R^{S6}$ is independently selected from (a) halo, (b1) $C_{1-6}$ aliphatic, (b2) $R^{\tilde{6}-3}$, (c) —OR*⁶, (d) —N(R*⁶)₂, (e) —SR†⁶, (f) $C_{1-3}$ haloalkyl, (h) —NO₂, (i) —CN, (j) —C(O)—R†⁶, (k) —C(O)—OR*⁶, (l) —C(O)—N(R*⁶)₂, (m) —O—C(O)—R†⁶, (n) —N(R*⁶)—C(O)—R†⁶, (o) —O—C(O)—OR*z, (p) —O—C(O)—N(R*⁶)₂, (q) —N(R*⁶)—C(O)—OR*⁶ (r) —N(R*⁶)—C(O)—N(R*⁶)₂, (aa) $C_{3-6}$ carbocyclyl, (bb) -A-($C_{3-6}$ carbocyclyl), (cc) 5- to 6-membered heterocyclyl, (dd) -A-(5- to 6-membered heterocyclyl), (ee) $C_6$ aryl, (ff) -A-($C_6$ aryl), (gg) 5- to 6-membered heteroaryl and (hh) -A-(5- to 6-membered heteroaryl); wherein each instance of A is independently selected from $C_{1-3}$ alkylene, $C_{0-2,0-2}$ heteroalkylene, —O—, —S—, —N(R*¹)— and —C(O)—; and wherein each of (aa)-(dd) is optionally substituted with 1-3 groups independently selected from (a) halo, (b1) $C_{1-2}$ aliphatic, (b2) $R^{\#2}$-1, (c) —OR*², (d) —N(R*²)₂ and (e) —SR†²; and wherein each of (ee)-(hh) is optionally substituted with 1-3 groups independently selected from (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S7}$ is independently selected from —H, (a) halo, (b1) $C_{1-4}$ aliphatic, (b2) $R^{\#4-2}$, (c) —OR*⁴, (d) —N(R*⁴)₂ and (e) —SR†⁴;

each instance of $R^{S8}$ is independently selected from —H, (a) halo, (b1) $C_{1-4}$ aliphatic, (b2) $R^{\tilde{4}-2}$, (c) —OR*⁴, (d) —N(R*⁴)₂, (e) —SR†⁴, (f) $C_{1-3}$ haloalkyl, (g1) $C_{1-3}$ haloalkoxy, (g2) $C_{1-3}$haloalkylthio, (h) —NO₂, (i) —CN, (j) —C(O)—R†⁴, (k) —C(O)—OR*⁴, (l) —C(O)—N(R*⁴)₂, (m) —O—C(O)—R†⁴, (n) —N(R*⁴)—C(O)—R†⁴, (o) —O—C(O)—OR*⁴, (p) —O—C(O)—N(R*⁴)₂, (q) —N(R*⁴)—C(O)—OR*⁴ and (r) —N(R*⁴)—C(O)—N(R*⁴)₂; and each instance of $R^{S9}$ is independently selected from —H, (a) halo, (b1) $C_{1-6}$ aliphatic, (b2) $R^{\tilde{6}-3}$ (c) —OR*⁶, (d) —N(R*⁶)₂, (e) —SR†⁶, (f) $C_{1-3}$ haloalkyl, (g1) $C_{1-3}$ haloalkoxy, (g2) $C_{1-4}$ haloalkylthio, (h) —NO₂, (i) —CN, (j) —C(O)—R†⁴, (k) —C(O)—OR*⁶, (l) —C(O)—N(R*⁶)₂, (m) —O—C(O)—R†⁶, (n) —N(R*⁶)—C(O)—R†⁶, (o) —O—C(O)—OR*⁶, (p) —O—C(O)—N(R*⁶)₂, (q) —N(R*⁶)—C(O)—OR*⁶, (r) —N(R*)—C(O)—N(R*⁶)₂, (s) —Si(R†²), (aa) $C_{3-8}$ carbocyclyl, (bb) -A-($C_{3-8}$ carbocyclyl), (cc) 5- to 10-membered heterocyclyl, (dd) -A-(5- to 10-membered heterocyclyl), (ee) $C_{6-10}$ aryl, (ff) -A-($C_{6-10}$ aryl), (gg) 5- to 10-membered heteroaryl and (hh) -A-(5- to 10-membered heteroaryl); wherein each instance of A is independently selected from $C_{1-3}$ alkylene, $C_{0-3,0-3}$ heteroalkylene, —O—, —S—, —N(R*¹)— and —C(O)—; and wherein each of (aa)-(dd) is optionally substituted with 1-3 groups independently selected from (a) halo, (b1) $C_{1-2}$ aliphatic, (b2) $R^{\#2-1}$, (c) —OR*², (d) —N(R*²)₂ and (e) —SR†²; and wherein each of (ee)-(hh) is optionally substituted with 1-3 groups independently selected from (a) halo, (b1) $C_{1-4}$ aliphatic, (b2) $R^{\#4-2}$, (c) —OR*⁴, (d) —N(R*⁴)₂ and (e) —SR†⁴.

Each instance of

| | | |
|---|---|---|
| $R^{*6}$ | | {$C_{1-6}$ alkyl |
| $R^{*4}$ | | {$C_{1-4}$ alkyl |
| $R^{*3}$ | is independently —H or | {$C_{1-3}$ alkyl |
| $R^{*2}$ | | {$C_{1-2}$ alkyl |
| $R^{*1}$ | | {methyl. |

Each instance of

| | | |
|---|---|---|
| $R^{\dagger 6}$ | | {$C_{1-6}$ alkyl |
| $R^{\dagger 4}$ | | {$C_{1-4}$ alkyl |
| $R^{\dagger 3}$ | is independently | {$C_{1-3}$ alkyl |
| $R^{\dagger 2}$ | | {$C_{1-2}$ alkyl. |

As prescribed in the following table, each instance of

| | | | | | |
|---|---|---|---|---|---|
| $R^{\tilde{6}-3}$ | | {$C_{1-6}$ alkyl} | | {1-3 | |
| $R^{\tilde{6}-2}$ | | {$C_{1-6}$ alkyl} | | {1-2 | |
| $R^{\tilde{6}-1}$ | is independently | {$C_{1-6}$ alkyl} | unsubstituted or | {1 | substituent(s): |
| $R^{\tilde{4}-2}$ | | {$C_{1-4}$ alkyl} | substituted with | {1-2 | |
| $R^{\tilde{4}-1}$ | | {$C_{1-4}$ alkyl} | | {1 | |
| $R^{\tilde{2}-1}$ | | {$C_{1-2}$ alkyl} | | {1 | |

| 1-3 | 1-2 | 1 |
|---|---|---|

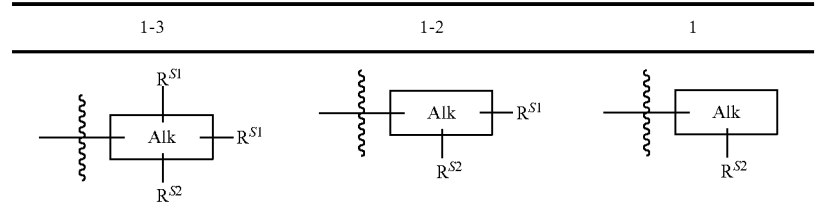

wherein represents the alkyl group.

As prescribed in the following table, each instance of

| | | | | |
|---|---|---|---|---|
| $R^{\#6-3}$ | | {$C_{1-6}$ alkyl} | {1-3 | |
| $R^{\#6-2}$ | | {$C_{1-6}$ alkyl} | {1-2 | |
| $R^{\#6-1}$ | is independently | {$C_{1-6}$ alkyl} | {1 | substituent(s): |
| $R^{\#4-2}$ | | {$C_{1-4}$ alkyl} unsubstituted or substituted with | {1-2 | |
| $R^{\#4-1}$ | | {$C_{1-4}$ alkyl} | {1 | |
| $R^{\#2-1}$ | | {$C_{1-2}$ alkyl} | {1 | |
| 1-3 | | 1-2 | | 1 |

[structures showing Alk group with $R^{S1}$ substituents in 1-3, 1-2, and 1 substitution patterns]

wherein —Alk— represents the alkyl group.

In each of these groups, when a subgroup is designating with a multiple occurrence, each occurrence is selected independently. For example, in —N(R*$^6$)$_2$, the R*$^6$ groups can be the same or different.

The following common names and abbreviations for various radicals are employed throughout.

| | | |
|---|---|---|
| methyl | Me | —CH$_3$ |
| ethyl | Et | —CH$_2$CH$_3$ |
| propyl | Pr | —CH$_2$CH$_2$CH$_3$ |
| isopropyl | $^i$Pr | CH$_3$CHCH$_3$ |
| butyl | Bu | —CH$_2$CH$_2$CH$_2$CH$_3$ |
| isobutyl | $^i$Bu | —CH$_2$CHCH$_3$ with CH$_3$ |
| sec-butyl | $^s$Bu | CH$_3$CHCH$_2$CH$_3$ |
| tert-butyl | $^t$Bu | —CCH$_3$ with CH$_3$, CH$_3$ |
| phenyl | Ph | [phenyl structure] |
| benzyl | Bn | [benzyl structure] |

Chemical Entities

Unless otherwise stated, structures depicted herein are meant to include chemical entities which differ only in the presence of one or more isotopically enriched atoms. For example, chemical entities having the present structure except for the replacement of a hydrogen atom by a deuterium or tritium, or the replacement of a carbon atom by a $^{13}$C- or $^{14}$C-enriched carbon are within the scope of the invention.

Unless stereochemical configuration is denoted, structures depicted herein are meant to include all stereochemical forms of the structure, i.e., the R and S configurations for each asymmetric center. Therefore, unless otherwise indicated, single stereochemical isomers as well as enantiomeric and diastereomeric mixtures of the present chemical entities are within the scope of the invention.

Each chemical entity of the present invention is a compound of Formula I:

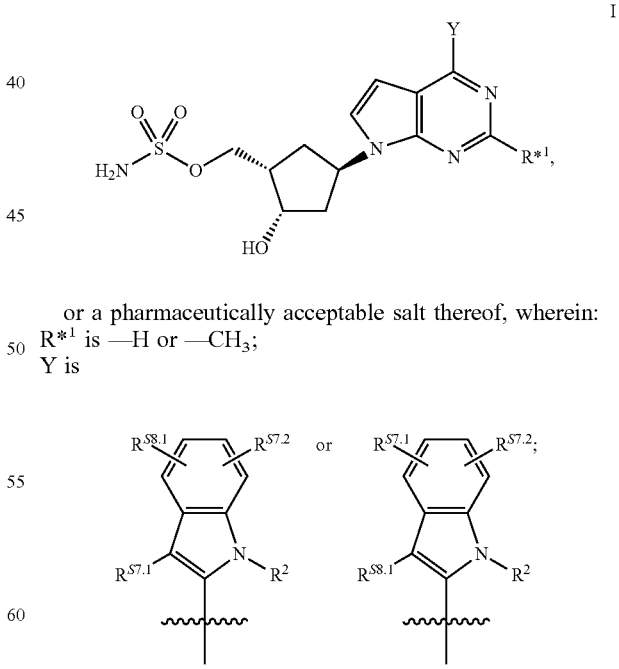

or a pharmaceutically acceptable salt thereof, wherein:
R*$^1$ is —H or —CH$_3$;
Y is

[two indole-type structures with $R^{S7.1}$, $R^{S7.2}$, $R^{S8.1}$, $R^2$ substituents]

R$^2$ is —H, —CH$_3$ or —C(=O)—R$^{†4}$;
each of R$^{S7.1}$ and R$^{S7.2}$ is independently —H, (a) halo, (b1) C$_{1-3}$ aliphatic, (b2) R$^{\#2-1}$, (c) —OR*$^3$, (d) —N(R*$^3$)$_2$ or (e) —SR$^{†3}$;

$R^{S8.1}$ is —H, (a) halo, (b1) $C_{1-4}$ aliphatic, (b2) $R^{\frown 4-2}$, (c) —OR*⁴, (d) —N(R*⁴)₂, (e) —SR†⁴, (f) $C_{1-3}$ fluoroalkyl, (g1) $C_{1-2}$ fluoroalkoxy, (g2) $C_{1-2}$ fluoroalkylthio, (h) —NO₂, (i) —CN, (j) —C(O)—R†⁴, (k) —C(O)—OR*⁴, (l) —C(O)—N(R*⁴)₂, (n) —N(R*⁴)—C(O)—R†⁴, (q) —N(R*⁴)—C(O)—OR*⁴ or (r) —N(R*⁴)—C(O)—N(R*⁴)₂;

provided that at least one of $R^{S7.1}$, $R^{S7.2}$ and $R^{S8.1}$ is —H.

each instance of R*⁴ is independently —H or $C_{1-4}$ alkyl;
each instance of R*³ is independently —H or $C_{1-3}$ alkyl;
each instance of R†⁴ is independently $C_{1-4}$ alkyl;
each instance of R†³ is independently $C_{1-3}$ alkyl;
each instance of $R^{\frown 4-2}$ is independently

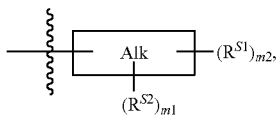

wherein

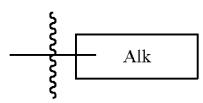

represents $C_{1-4}$ alkyl; and
each of m1 and m2 is independently 0 or 1;
each instance of $R^{\#2-1}$ is independently

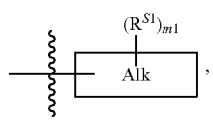

wherein

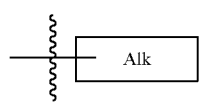

represents $C_{1-2}$ alkyl; and
m1 is 0 or 1.
each instance of $R^S$ is independently —H, (a) halo, (c) —OR*², (d) —N(R*²)₂ or (e) —SR†²; and
each instance of $R^2$ is independently —H, (a) halo, (c) —OR*², (d) —N(R*²)₂, (e) —SR†² (h) —NO₂, (i) —CN, (j) —C(O)—R†², (k) —C(O)—OR*², (l) —C(O)—N(R*²)₂, (m) —O—C(O)—R†² (n) —N(R*²)—C(O)—R†², (o) —O—C(O)—OR*², (p) —O—C(O)—N(R*²)₂, (q) —N(R*²)—C(O)—OR*² or (r) —N(R*²)—C(O)—N(R*²)₂;
each instance of R*² is independently —H or $C_{1-2}$ alkyl; and
each instance of R†² is independently $C_{1-2}$ alkyl.

In some embodiments
$R^{S8.1}$ is —H, (a) halo, (b1) $C_{1-4}$ aliphatic, (b2) $R^{\frown 4-2}$, (f) $C_{1-3}$ fluoroalkyl, (h) —NO₂, (i) —CN, (j) —C(O)—R†⁴, (k) —C(O)—OR*⁴ or (l) —C(O)—N(R*⁴)₂; and each instance of $R^{\#4-2}$ is independently

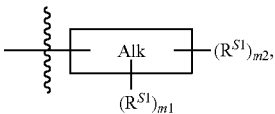

wherein

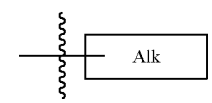

represents $C_{1-4}$ alkyl; and
each of m1 and m2 is independently 0 or 1.

In some embodiments, each of $R^{S7.1}$ and $R^{S72}$ is independently —H, (a) halo, (b1) $C_{1-3}$ aliphatic or (c) —OR*³; and $R^{S8.1}$ is —H, (f) $C_{1-3}$ fluoroalkyl or (i) —CN. In some embodiments, each of $R^{S7.1}$ and $R^{S7.2}$ is independently —H, (a) —F, Cl, (b1) —CH₃ or (c) —OCH₃; and $R^{S8.1}$ is —H, (f) —CF₃ or (i) —CN.

In some embodiments, Y is

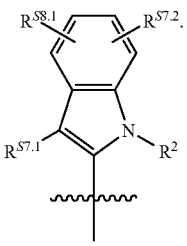

In some embodiments, $R^2$ is —H. In some embodiments, $R^2$ is —C(=O)—O$^t$Bu.

In some embodiments, R*¹ is —H. In some embodiments, R*¹ is —CH₃.

In some embodiments, at least two of $R^{S7.1}$, $R^{S7.2}$ and $R^{S8.1}$ are —H.

In some embodiments, $R^{S7.1}$, $R^{S7.2}$ and $R^{S8.1}$ are —H.

Examples of compounds of the chemical entities of the present invention include those listed in the following tables.

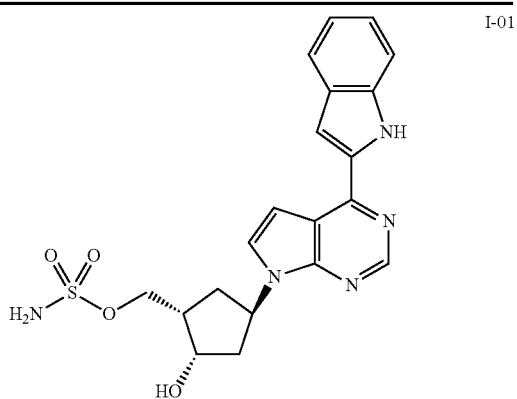

I-01

-continued
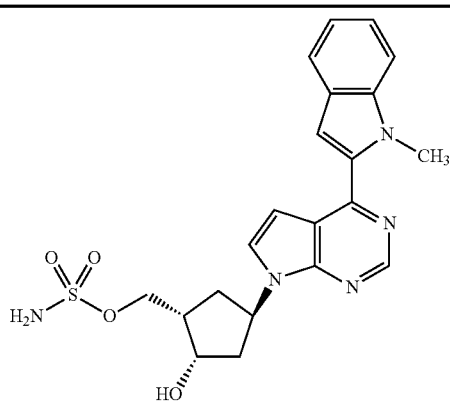
I-02
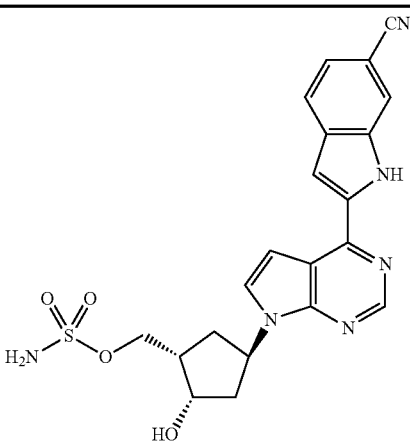
I-05
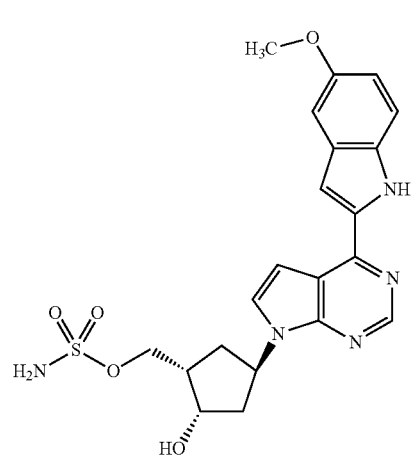 [SMILES: COc1ccc2[nH]c(-c3ncnc4c3ccn4[C@@H]3C[C@@H](COS(N)(=O)=O)[C@@H](O)C3)cc2c1]
I-03
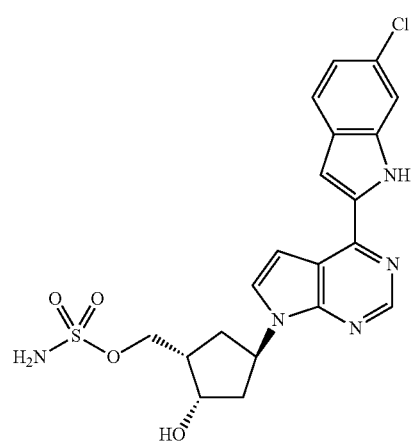 [SMILES: NS(=O)(=O)OC[C@@H]1C[C@@H](n2ccc3c(-c4cc5ccc(Cl)cc5[nH]4)ncnc32)C[C@@H]1O]
I-04
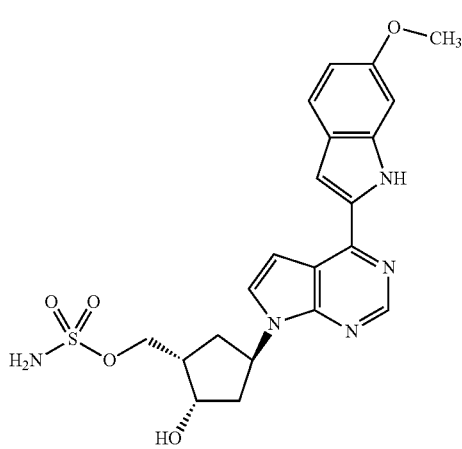 [SMILES: COc1ccc2cc(-c3ncnc4c3ccn4[C@@H]3C[C@@H](COS(N)(=O)=O)[C@@H](O)C3)[nH]c2c1]
I-07

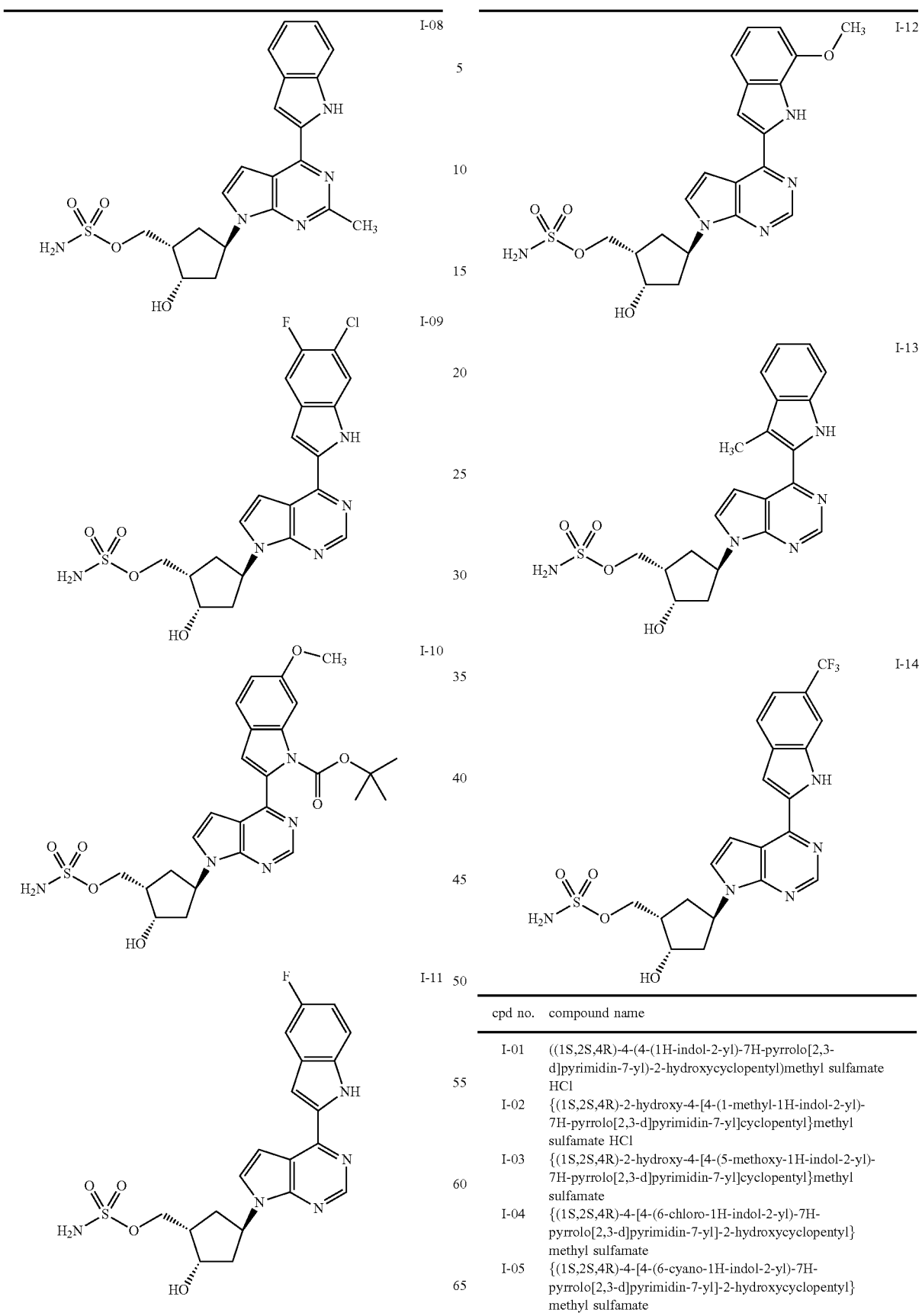

| cpd no. | compound name |
|---|---|
| I-01 | ((1S,2S,4R)-4-(4-(1H-indol-2-yl)-7H-pyrrolo[2,3-d]pyrimidin-7-yl)-2-hydroxycyclopentyl)methyl sulfamate HCl |
| I-02 | {(1S,2S,4R)-2-hydroxy-4-[4-(1-methyl-1H-indol-2-yl)-7H-pyrrolo[2,3-d]pyrimidin-7-yl]cyclopentyl}methyl sulfamate HCl |
| I-03 | {(1S,2S,4R)-2-hydroxy-4-[4-(5-methoxy-1H-indol-2-yl)-7H-pyrrolo[2,3-d]pyrimidin-7-yl]cyclopentyl}methyl sulfamate |
| I-04 | {(1S,2S,4R)-4-[4-(6-chloro-1H-indol-2-yl)-7H-pyrrolo[2,3-d]pyrimidin-7-yl]-2-hydroxycyclopentyl}methyl sulfamate |
| I-05 | {(1S,2S,4R)-4-[4-(6-cyano-1H-indol-2-yl)-7H-pyrrolo[2,3-d]pyrimidin-7-yl]-2-hydroxycyclopentyl}methyl sulfamate |

| | |
|---|---|
| I-06 | {(1S,2S,4R)-2-hydroxy-4-[4-(6-methyl-1H-indol-2-yl)-7H-pyrrolo[2,3-d]pyrimidin-7-yl]cyclopentyl}methyl sulfamate |
| I-07 | {(1S,2S,4R)-2-hydroxy-4-[4-(6-methoxy-1H-indol-2-yl)-7H-pyrrolo[2,3-d]pyrimidin-7-yl]cyclopentyl}methyl sulfamate |
| I-08 | {(1S,2S,4R)-2-hydroxy-4-[4-(1H-indol-2-yl)-2-methyl-7H-pyrrolo[2,3-d]pyrimidin-7-yl]cyclopentyl}methyl sulfamate HCl |
| I-09 | {(1S,2S,4R)-4-[4-(6-chloro-5-fluoro-1H-indol-2-yl)-7H-pyrrolo[2,3-d]pyrimidin-7-yl]-2-hydroxycyclopentyl}methyl sulfamate |
| I-10 | tert-butyl 2-(7-{(1R,3S,4S)-3-hydroxy-4-[(sulfamoyloxy)methyl]cyclopentyl}-7H-pyrrolo[2,3-d]pyrimidin-4-yl)-6-methoxy-1H-indole-1-carboxylate |
| I-11 | {(1S,2S,4R)-4-[4-(5-fluoro-1H-indol-2-yl)-7H-pyrrolo[2,3-d]pyrimidin-7-yl]-2-hydroxycyclopentyl}methyl sulfamate |
| I-12 | {(1S,2S,4R)-2-hydroxy-4-[4-(7-methoxy-1H-indol-2-yl)-7H-pyrrolo[2,3-d]pyrimidin-7-yl]cyclopentyl}methyl sulfamate |
| I-13 | {(1S,2S,4R)-2-hydroxy-4-[4-(3-methyl-1H-indol-2-yl)-7H-pyrrolo[2,3-d]pyrimidin-7-yl]cyclopentyl}methyl sulfamate |
| I-14 | [(1S,2S,4R)-2-hydroxy-4-{4-[6-(trifluoromethyl)-1H-indol-2-yl]-7H-pyrrolo[2,3-d]pyrimidin-7-yl}cyclopentyl]methyl sulfamate |

These and other compounds of the chemical entities of the present invention can be made with reference to the procedures described in the Examples.

The chemical entities of this invention are useful inhibitors of Uba6 activity. Inhibitors are meant to include chemical entities which reduce the promoting effects of Uba6 initiated conjugation of either ubiquitin or FAT10 to target proteins (e.g., reduction of ubiquitination), reduce intracellular signaling mediated by either ubiquitin or FAT10 conjugation, and/or reduce proteolysis mediated by either ubiquitin or FAT10 conjugation (e.g., inhibition of either cellular ubiquitin or FAT10 conjugation, ubiquitin or FAT10 dependent signaling and ubiquitin or FAT10 dependent proteolysis). Thus, the chemical entities of this invention may be assayed for their ability to inhibit Uba6 in vitro or in vivo, or in cells or animal models according to methods provided in further detail herein, or methods known in the art. The chemical entities may be assessed for their ability to bind or modulate Uba6 activity directly. Alternatively, the activity of the chemical entities may be assessed through indirect cellular assays, or assays measuring downstream effects of Uba6 promoted ubiquitin or FAT10 activation to assess inhibition of downstream effects of Uba6 inhibition (e.g., inhibition of ubiquitin or FAT10 dependent proteolysis). For example, activity may be assessed by detection of either ubiquitin or FAT10 conjugated substrates (e.g., ubiquitin or FAT10 charged Use1 or ubiquitinated or fatylated substrates); detection of downstream protein substrate stabilization (e.g., stabilization of N-end rule substrates); detection of downstream effects of Uba6 inhibition and substrate stabilization (e.g., reporter assays). Assays for assessing activities are described below in the Examples section and/or are known in the art.

Compositions

Some embodiments of this invention relate to a composition comprising a chemical entity of this invention and a pharmaceutically acceptable carrier.

If a pharmaceutically acceptable salt is the chemical entity of the invention utilized in these compositions, the salts preferably are derived from inorganic or organic acids and bases. For reviews of suitable salts, see, e.g., Berge et al, *J. Pharm. Sci.* 66:1-19 (1977) and *Remington: The Science and Practice of Pharmacy,* 20th Ed.; A. Gennaro (ed.), Lippincott Williams & Wilkins (2000) ("*Remington's*").

Examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Examples of suitable base addition salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The pharmaceutical compositions of the invention preferably are in a form suitable for administration to a recipient subject, preferably a mammal, more preferably a human. The term "pharmaceutically acceptable carrier" is used herein to refer to a material that is compatible with the recipient subject, and is suitable for delivering an active agent to the target site without terminating the activity of the agent. The toxicity or adverse effects, if any, associated with the carrier preferably are commensurate with a reasonable risk/benefit ratio for the intended use of the active agent. Many such pharmaceutically acceptable carriers are known in the art. See, e.g., *Remington's; Handbook of Pharmaceutical Excipients,* 6th Ed., R. C. Rowe et al. (eds.), Pharmaceutical Press (2009).

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutically acceptable carriers that may be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Pharmaceutical formulations may be prepared as liquid suspensions or solutions using a liquid, such as an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons such as mineral oil and petrolatum; and water may also be used in suspension formulations.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents may also be added. In such solid dosage forms, the active chemical entity is mixed with at least one inert, pharmaceutically acceptable excipient or carrier such as sodium citrate or dicalcium phosphate and/or a) fillers or extenders such as starches, lactose, sucrose, glucose, mannitol, micro-crystalline cellulose and silicic acid, b) binders such as, for example, carboxymethylcellulose, alginates, gelatin, sucrose, and acacia, c) humectants such as glycerol, d) disintegrating agents such as agar-agar, calcium carbonate, polyvinylpyrrolidinone, croscarmellose, sodium starch glycolate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, sodium stearyl fumarate, solid polyethylene glycols, sodium lauryl sulfate, silicon dioxide and mixtures thereof. In the case of capsules, tablets and pills, the dosage form may also comprise buffering agents.

The active chemical entity can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of this invention are particularly useful in therapeutic applications relating to disorders as described herein (e.g., proliferation disorders, e.g., cancers, inflammatory, neurodegenerative disorders). The term "subject" as used herein, means an animal, preferably a mammal, more preferably a human. The term "patient" as used herein, means a human. Preferably, the composition is formulated for administration to a patient or subject having or at risk of developing or experiencing a recurrence of the relevant disorder being treated. Preferred pharmaceutical compositions of the invention are those formulated for oral, intravenous, or subcutaneous administration. However, any of the above dosage forms containing a therapeutically effective amount of a chemical entity of the invention are well within the bounds of routine experimentation and therefore, well within the scope of the instant invention. In certain embodiments, the pharmaceutical composition of the invention may further comprise another therapeutic agent. Preferably, such other therapeutic agent is one normally administered to patients with the disorder, disease or condition being treated.

By "therapeutically effective amount" is meant an amount of the chemical entity or composition sufficient, upon single or multiple dose administration, to cause a detectable decrease in Uba6 activity and/or the severity of the disorder or disease state being treated. "Therapeutically effective amount" is also intended to include an amount sufficient to treat a cell, prolong or prevent advancement of the disorder or disease state being treated (e.g., prevent additional tumor growth of a cancer, prevent additional inflammatory response), ameliorate, alleviate, relieve, or improve a subject's symptoms of the a disorder beyond that expected in the absence of such treatment. The amount of Uba6 inhibitor required will depend on the particular compound of the composition given, the type of disorder being treated, the route of administration, and the length of time required to treat the disorder. It should also be understood that a specific dosage and treatment regimen for any particular patient will depend upon a variety of factors, including the activity of the specific chemical entity employed, the age, body weight, general health, sex, and diet of the patient, time of administration, rate of excretion, drug combinations, the judgment of the treating physician, and the severity of the particular disease being treated. In certain aspects where the inhibitor is administered in combination with another agent, the amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

Uses

In some embodiments, the invention relates to a method of inhibiting or decreasing Uba6 activity in a sample comprising contacting the sample with a chemical entity of this invention, or composition comprising a chemical entity of the invention. The sample, as used herein, includes sample comprising purified or partially purified Uba6, cultured cells or extracts of cell cultures; biopsied cells or fluid obtained from a mammal, or extracts thereof; and body fluid (e.g., blood, serum, saliva, urine, feces, semen, tears) or extracts thereof. Inhibition of Uba6 activity in a sample can be carried out in vitro or in vivo, in cellulo, or in situ. In some embodiments, inhibition of Uba6 activity in a sample is carried out in vitro.

In some embodiments, the invention provides a method for treating a patient having a disorder, a symptom of a disorder, at risk of developing, or experiencing a recurrence of a disorder, comprising administering to the patient a chemical entity or pharmaceutical composition according to the invention. Treating can be to cure, heal, alleviate, relieve, alter, remedy, ameliorate, palliate, improve or affect the disorder, the symptoms of the disorder or the predisposition toward the disorder. While not wishing to be bound by theory, treating is believed to cause the inhibition of growth, ablation, or killing of a cell or tissue in vitro or in vivo, or otherwise reduce capacity of a cell or tissue (e.g., an aberrant cell, a diseased tissue) to mediate a disorder, e.g., a disorder as described herein (e.g., a proliferative disorder, e.g., a cancer, inflammatory disorder). As used herein, "inhibiting the growth" or "inhibition of growth" of a cell or tissue (e.g., a proliferative cell, tumor tissue) refers to slowing, interrupting, arresting or stopping its growth and metastases and does not necessarily indicate a total elimination of growth.

Uba6 represents a novel protein homeostasis target opportunity for the treatment of cancer and other human diseases where ubiquitin or FAT10 biology is present. Disease applications include those disorders in which inhibition of Uba6 activity is detrimental to survival and/or expansion of diseased cells or tissue (e.g., cells are sensitive to Uba6 inhibition; inhibition of Uba6 activity disrupts disease mechanisms; reduction of Uba6 activity stabilizes protein which are inhibitors of disease mechanisms; reduction of Uba6 activity results in inhibition of proteins which are activators of disease mechanisms). Disease applications are also intended to include any disorder, disease or condition which requires effective ubiquitination or fatylation activity, which activity can be regulated by diminishing Uba6 activity.

For example, methods of the invention are useful in treatment of disorders involving cellular proliferation, including disorders which require effective ubiquitin or FAT10 ligase dependent ubiquitination or fatylation and signaling or proteolysis (e.g., the ubiquitin proteasome pathway) for maintenance and/or progression of the disease state. The methods of the invention are useful in treatment of disorders mediated via proteins which are regulated by Uba6 activity. Relevant disorders include proliferative disorders, most notably cancers and inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis), vascular proliferative disorders (e.g., atherosclerosis, restenosis) autoimmune diseases (e.g., multiple sclerosis, tissue and organ rejection)); as well as inflammation associated with infection (e.g., immune responses), neurodegenerative disorders (e.g., Alzheimer's disease, Parkinson's disease, motor neuron disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies).

The chemical entities and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes solid tumors and bloodborne tumors. The term "cancer" encompasses diseases of skin, tissues, organs, bone, cartilage, blood, and vessels. The term "cancer" further encompasses primary and metastatic cancers.

In some embodiments, therefore, the invention provides the chemical entity of formula I, or a pharmaceutically acceptable salt thereof, for use in treating cancer. In some embodiments, the invention provides a pharmaceutical composition (as described herein) for the treatment of cancer comprising the chemical entity of formula I, or a pharmaceutically acceptable salt thereof. In some embodiments, the invention provides the use of the chemical entity of formula I, or a pharmaceutically acceptable salt thereof, for the preparation of a pharmaceutical composition (as described herein) for the treatment of cancer. In some embodiments, the invention provides the use of an effective amount of the chemical entity of formula I, or a pharmaceutically acceptable salt thereof, for the treatment of cancer. In some embodiments, the invention provides the chemical entity of formula I, or a pharmaceutically acceptable salt thereof, for the preparation of a medicament for use in treating cancer.

In some embodiments, the cancer is a solid tumor. Examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), small cell lung cancer, bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some embodiments, the cancer is a hematologic malignancy. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes. Other examples of hematologic malignancies include amyloidosis.

Depending on the particular disorder or condition to be treated, in some embodiments, the Uba6 inhibitor of the invention is administered in conjunction with additional therapeutic agent or agents. In some embodiments, the additional therapeutic agent(s) is one that is normally administered to patients with the disorder or condition being treated. As used herein, additional therapeutic agents that are normally administered to treat a particular disorder or condition are known as "appropriate for the disorder or condition being treated."

The Uba6 inhibitor of the invention may be administered with the other therapeutic agent in a single dosage form or as a separate dosage form. When administered as a separate dosage form, the other therapeutic agent may be administered prior to, at the same time as, or following administration of the Uba6 inhibitor of the invention.

In some embodiments, the Uba6 enzyme inhibitor of the invention is administered in conjunction with a therapeutic agent selected from cytotoxic agents, radiotherapy, and immunotherapy appropriate for treatment of proliferative disorders and cancer. Examples of cytotoxic agents suitable for use in combination with the Uba6 inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; including, e.g., CC-5013 and CC-4047; protein tyrosine kinase inhibitors, including, e.g., imatinib mesylate and gefitinib; proteasome inhibitors, including, e.g., bortezomib; thalidomide and related analogs; antibodies, including, e.g., trastuzumab, rituximab, cetuximab, and bevacizumab; mitoxantrone; dexamethasone; prednisone; and temozolomide.

Other examples of agents the inhibitors of the invention may be combined with include anti-inflammatory agents such as corticosteroids, TNF blockers, II-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophosphamide, azathioprine, methotrexate, and sulfasalazine; antibacterial and antiviral agents; and agents for Alzheimer's treatment such as donepezil, galantamine, memantine and rivastigmine.

Eliminating the function of proteins required for cholesterol biosynthesis and homeostasis is used for lowering lipid levels in patients affected by hypercholesterolemia, metabolic syndrome and coronary heart disease amongst others. Individual enzymes, such as hydroxymethylglutaryl-CoA reductase, squalene synthase and squalene epoxidase (L. Trapani, et al., *IUMB* Life, 2011, 63(11), 964-71; S. Seiki, et al., *Cardiol. Rev.* 2009, 17(2), 70-6; A. Belter, et al., *Biol. Chem.* 2011, 392(12), 1053-75) or suppressing the SREBP-dependent biosynthetic pathway have been targeted (L. Zhang, *Int. J. Biol. Sci.*, 2012, 8(3), 310-27.) In some embodiments, the compounds of the present invention are useful in the treatment of those metabolic disorders where lowering lipid levels is indicated.

In order that this invention is more fully understood, the following preparative and testing examples are set forth. These examples are for the purpose of illustration only and are not intended to be construed as limiting the scope of the invention in any way.

EXAMPLES

Abbreviations

AA ammonium acetate
ACN acetonitrile
d doublet
DCM dichloromethane
dd doublet of doublets
DMF N, N-dimethylformamide
DMSO dimethylsulfoxide
dt doublet of triplets
EtOAc ethyl acetate
FA formic acid
J coupling constant
HPLC high performance liquid chromatography
h hours
Hz hertz
LAH lithium aluminum hydride
LCMS liquid chromatography mass spectrum
LDA lithium diisopropylamide
m multiplet
M molar
MeOH methanol
min minutes
RT room temperature
s singlet
t triplet
THF tetrahydrofuran
q quartet Analytical Methods LCMS data were obtained using an Agilant 1100 LC (column: Waters Symmetry, 3.5 μm C18 100×4.6 mm) and a Waters ZQ MS.

Preparative HPLC is performed using a Phenominex Luna C18 column.

NMR spectrum is shown by proton NMR, using a 300 MHz Bruker Avance spectrometer equipped with a 5 mm QNP probe and a 400 MHz Bruker Avance II spectrometer equipped with a 5 mm QNP probe for the measurement; δ values are expressed in ppm.

Synthetic Methods

Example 1

Synthesis of (1S,2S,4R)-4-amino-2-(hydroxymethyl)cyclopentanol HBr Salt

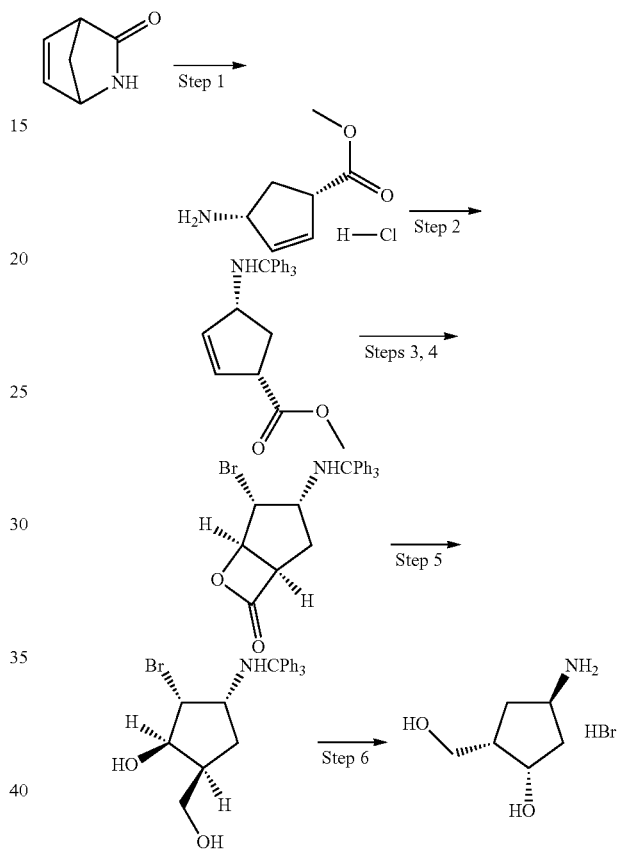

The title compound is prepared according to Armitage et al., U.S. Patent Appl. Publ., No. 2009/0036678 (publd. Feb. 5, 2009), Intl. Patent Appl. Publ. No. WO 20091042013 (publd. Apr. 2, 2009), which is hereby incorporated by reference herein for the teachings of this synthesis.

Example 2

Synthesis of (4,6-dichloropyrimidin-5-yl)acetaldehyde

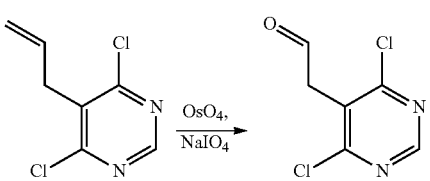

5-Allyl-4,6-dichloropyrimidine (see Montgomery, J. A. and Hewson, K., *J. Med. Chem.* 1967, 10, 665-667) (2.00 g, 10.6 mmol) was dissolved in THF (16 mL). Osmium tetraoxide (30 mg, 0.10 mmol) was added and after a few min, the reaction mixture turned very dark. Sodium metaperiodate (4.75 g, 22.2 mmol) was then added in portions over 34 min and the reaction mixture temperature was maintained at 20-22° C. The solids were removed by filtration and were washed well with THF (2×5 mL). Saturated brine was added to the filtrate and the phases were separated. The aqueous phase was saturated with solid sodium chloride and the phases separated. The aqueous phase was extracted with additional EtOAc (2×10 mL). The organic extracts were combined and concentrated under reduced pressure. The crude residue was dried in vacuo and the title compound was isolated as a gray solid (2.00 g, 99% yield).

$^1$H NMR (300 MHz, CDCl$_3$) δ 9.80 (s, 1H), 8.74 (s, 1H) and 4.14 (s, 2H).

(4,6-Dichloro-2-methylpyrimidin-5-yl)acetaldehyde ($^1$H NMR (300 MHz, d$_6$-DMSO) δ 9.71 (s, 1H), 4.16 (s, 2H), 2.60 (s, 3H).) and (4,6-dichloro-2-ethylpyrimidin-5-yl)acetaldehyde ($^1$H NMR (300 MHz, CDCl$_3$) δ 9.78 (s, 1H), 4.11 (d, J=10.8 Hz, 2H), 2.95 (q, J=7.6 Hz, 2H) and 1.36 (t, J=7.6 Hz, 3H)) were both prepared as described above utilizing the appropriate amidine derivatives to prepare the appropriate allyl dichloropyrimidines (see Montgomery, J. A. and Hewson, K., *J. Med. Chem.* 1967, 10, 665-667).

Example 3

Synthesis of (1S,2S,4R)-4-(4-chloro-7H-pyrrolo[2,3-d]pyrimidin-7-yl)-2-(hydroxymethyl)cyclopentanol

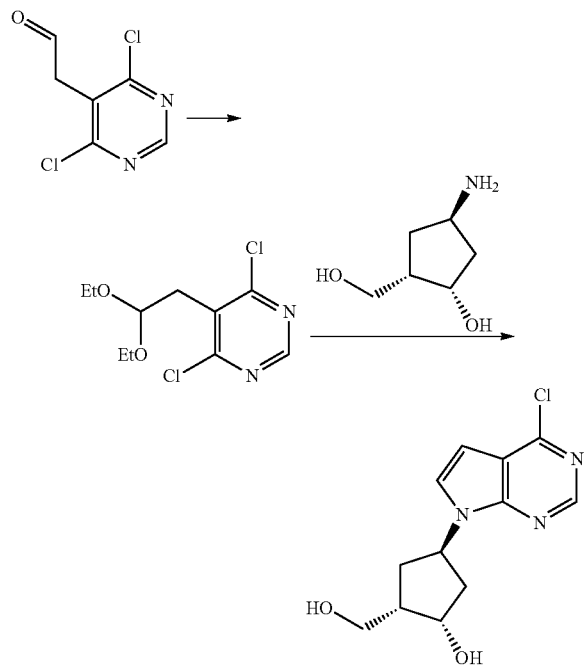

Step 1:
4,6-dichloro-5-(2,2-diethoxyethyl)pyrimidine (4,6-Dichloropyrimidin-5-yl)acetaldehyde (500.0 g, 2.618 mol) and ammonium chloride (14.0 g, 0.262 mol) were suspended in absolute ethanol (4.02 L, 68.9 mol). The suspension was heated to 85° C. and monitored by NMR sampling after 2 h and then hourly. After 5 h, $^1$H NMR indicated reaction was mostly complete (ca. 5% starting aldehyde remaining). The reaction mixture was cooled to ambient temperature and the mixture was stirred with activated charcoal (80 g) for 10 min and then filtered through Celite® 545. The bed was washed with absolute ethanol (500 mL). The solvent was then removed under reduced pressure and the residue was dissolved in DCM (4.02 L) and then washed with water (2.4 L) and brine (2.4 L). The organic phase was then dried over sodium sulfate, and filtered through Celite®545, concentrated under reduced pressure and then further dried in a vacuum oven at 25° C. for approximately 88 h. This yielded 4,6-dichloro-5-(2,2-diethoxyethyl)pyrimidine as an amber oil (670 g, 96% yield). $^1$H NMR (300 MHz, d$_6$-DMSO) δ 8.82-8.71 (m, 1H), 3.60 (dq, J=9.6, 7.0 Hz, 2H), 3.39 (dq, J=9.6, 7.0 Hz, 2H), 3.13 (dd, J=5.6, 3.1 Hz, 2H) and 1.00 (dd, J=8.1, 6.0 Hz, 6H).

Step 2: (1 S,2S,4R)-4-(4-chloro-7H-pyrrolo[2,3-d]pyrimidin-7-yl)-2-(hydroxymethyl)cyclopentanol To a slurry of 4,6-dichloro-5-(2,2-diethoxyethyl)pyrimidine (860 mg, 3.25 mmol) and (1S,2S,4R)-4-amino-2-(hydroxymethyl)cyclopentanol.HBr (865 mg, 4.08 mmol) in isopropyl alcohol (7.1 mL) and water (0.95 mL), triethylamine (1.13 mL, 8.11 mmol) was added. This mixture was then heated to 85° C. for 23 h. The mixture was cooled to 50° C. and hydrochloric acid (4M in water, 1.6 mL) was added slowly. The resulting mixture was then stirred at 50° C. for 2 h. The reaction mixture was cooled to ambient temperature and sodium bicarbonate (0.8 g, 10 mmol) was added. EtOAc (12 mL) was added, followed by the addition of a half-saturated NaHCO$_3$ solution. The organic phase was isolated and the aqueous phase was extracted with EtOAc (2×. The organic phases were combined, washed once with brine, dried (Na$_2$SO$_4$) and concentrated to yield (1S,2S,4R)-4-(4-chloro-7H-pyrrolo[2,3-d]pyrimidin-7-yl)-2-(hydroxymethyl)cyclopentanol as a brown solid (850 mg, 98%). $^1$H NMR (300 MHz, CD$_3$OD) δ 8.56 (s, 1H), 7.67 (d, 1H), 6.65 (d, 1H), 5.52 (m, 1H), 4.50 (m, 1H), 3.79 (m, 1H), 3.66 (m, 1H), 2.63 (m, 1H), 2.25 (m, 3H) and 2.02 (m, 1H).

Example 3a

Synthesis of (1S,2S,4R)-4-(4-chloro-2-methyl-7H-pyrrolo[2,3-d]pyrimidin-7-yl)-2-(hydroxymethyl)cyclopentanol

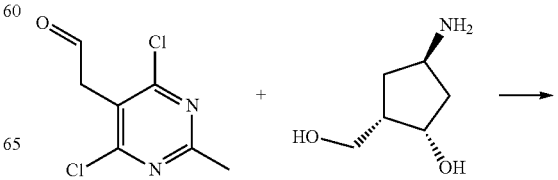

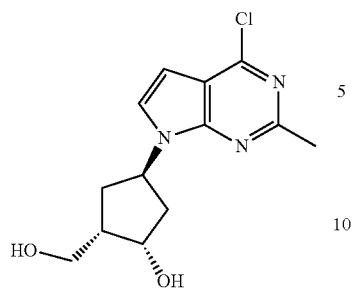

(4,6-Dichloro-2-methylpyrimidin-5-yl)acetaldehyde (0.46 g, 2.2 mmol), (1S,2S,4R)-4-amino-2-(hydroxymethyl)cyclopentanolo.HBr (0.500 g, 2.36 mmol;), isopropyl alcohol (21 mL, 280 mmol), and triethylamine (0.626 mL, 4.491 mmol) were combined and stirred at 75° C. overnight. A precipitate formed as the reaction proceeded. The mixture was cooled to room temperature and the precipitate removed by filtration. The filtrate was concentrated under reduced pressure. Purification by column chromatography (SiO$_2$, 1-7% MeOH in DCM) provided 0.342 g of the title compound (54% with some triethylammonium salt contamination). $^1$H NMR (300 MHz, CDCl$_3$) δ 7.17 (d, J=3.7 Hz, 1H), 6.54 (d, J=3.6 Hz, 1H), 5.49 (ddd, J=16.9, 8.6, 5.9 Hz, 1H), 4.76-4.67 (m, 1H), 4.00 (dt, J=11.0, 4.3 Hz, 1H), 3.92-3.81 (m, 1H), 2.74 (s, 3H), 2.71-2.59 (m, 1H), 2.46-2.30 (m, 4H), 2.18 (dd, J=5.8, 4.5 Hz, 1H) and 2.10-1.97 (m, 1H).

Example 4

Synthesis of [(1S,2S,4R)-2-{[tert-butyl(dimethyl)silyl]oxy}-4-(4-chloro-2-methyl-7H-pyrrolo[2,3-d]pyrimidin-7-yl)cyclopentyl]methanol

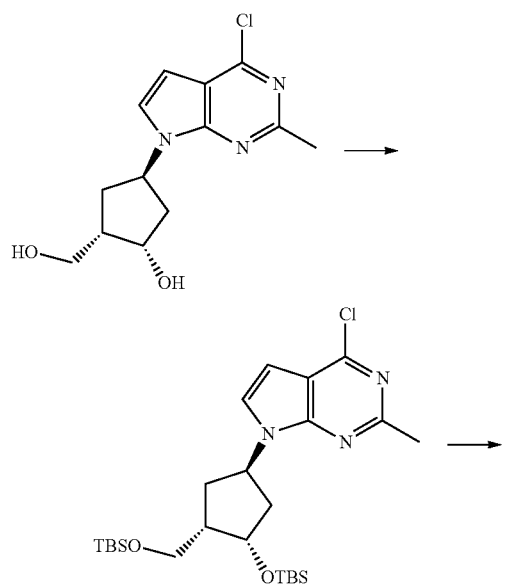

Step 1: 7-[(1R,3S,4S)-3-([Tert-butyl(dimethyl)silyl]oxy)-4-({[tert-butyl(dimethyl)silyl]oxy}methyl)-cyclopentyl]-4-chloro-2-methyl-7H-pyrrolo[2,3-d]pyrimidine (1S,2S,4R)-4-(4-Chloro-2-methyl-7H-pyrrolo[2,3-d]pyrimidin-7-yl)-2-(hydroxymethyl)cyclopentanol (0.426 g, 1.51 mmol) was dissolved in DMF (12.0 mL) and tert-butyldimethylsilyl chloride (0.912 g, 6.05 mmol), 1H-imidazole (0.412 g, 6.05 mmol) and N,N-dimethylaminopyridine (0.092 g, 0.76 mmol) were added sequentially. The reaction mixture was stirred overnight at RT and then concentrated under reduced pressure to remove % of the DMF. The remaining mixture was partitioned between EtOAc (100 mL) and water (50 mL). The aqueous phase was extracted with EtOAc (50 mL). The combined organic extracts were washed with water (2×75 mL) and brine, dried over sodium sulfate, filtered and concentrated under reduced pressure. Purification by column chromatography (SiO$_2$, 0-15 EtOAc/hexanes) provided 7-[(1R,3S,4S)-3-{[tert-butyl(dimethyl)silyl]oxy}-4-({[tert-butyl(dimethyl)silyl]oxy}methyl)cyclopentyl]-4-chloro-7H-pyrrolo[2,3-d]pyrimidine (0.361 g, 47%). $^1$H NMR (300 MHz, CDCl$_3$) δ 7.18 (d, J=3.6 Hz, 1H), 6.53 (d, J=3.6 Hz, 1H), 5.43 (ddd, J=18.0, 8.3, 4.8 Hz, 1H), 4.50 (s, 1H), 3.79 (dd, J=10.0, 7.2 Hz, 1H), 3.62 (dd, J=10.0, 6.8 Hz, 1H), 2.74 (s, 3H), 2.50 (dd, J=9.7, 6.2 Hz, 1H), 2.36-2.03 (m, 3H), 1.95 (ddd, J=13.6, 8.9, 4.7 Hz, 1H), 0.98-0.91 (m, 9H), 0.90 (d, J=2.8 Hz, 9H), 0.09 (t, J=2.5 Hz, 6H), 0.07 (s, 6H).

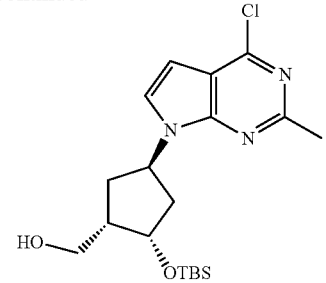

Step 2: [(1S,2S,4R)-2-{[tert-butyl(dimethyl)silyl]oxy}-4-(4-chloro-2-methyl-7H-pyrrolo[2,3-d]pyrimidin-7-yl)cyclopentyl]methanol 7-[(1R,3S,4S)-3-{[Tert-butyl(dimethyl)silyl]oxy}-4-({[tert-butyl(dimethyl)silyl]oxy}methyl)cyclopentyl]-4-chloro-7H-pyrrolo[2,3-d]pyrimidine (1.00 g, 2.02 mmol) was dissolved in ethanol (10 mL) and the solution was cooled to −78° C. HCl (as a mixture of 1% by volume conc. HCl in absolute EtOH at 0° C., 33.4 mL, 4.03 mmol) was added and the reaction mixture was kept in the freezer (−24° C.) for 26 h. The reaction mixture was cooled to −78° C. and a saturated solution of sodium bicarbonate was added. The mixture was extracted with EtOAc (3×). The combined organic phases were washed with water and brine, dried over sodium sulfate, filtered and concentrated under reduced pressure. Purification by column chromatography (SiO$_2$, 0-70% elution with EtOAc/hexanes) provided [(1S,2S,4R)-2-{[tert-butyl(dimethyl)silyl]oxy}-4-(4-chloro-2-methyl- 7H-pyrrolo[2,3-d]pyrimidin-7-yl)cyclopentyl]methanol as a clear oil (0.716 g, 93% yield). ¹H NMR (300 MHz, CDCl₃) δ 7.16 (d, J=3.6 Hz, 1H), 6.53 (d, J=3.6 Hz, 1H), 5.45-5.31 (m, 1H), 4.67 (dd, J=8.1, 4.6 Hz, 1H), 3.88-3.73 (m, 2H), 2.74 (s, 3H), 2.65-2.52 (m, 1H), 2.46-2.33 (m, 2H), 2.31-2.24 (m, 2H), 2.12-1.99 (m, 1H), 0.95 (s, 9H) and 0.14 (d, J=0.9 Hz, 6H).

[(1 S,2S,4R)-2-{[tert-butyl(dimethyl)silyl]oxy}-4-(4-chloro-7H-pyrrolo[2,3-d]pyrimidin-7-yl)-cyclopentyl]methanol (¹H NMR (300 MHz, CDCl₃) δ 8.62 (s, 1H), 7.27 (d, J=3.3 Hz, 1H), 6.60 (d, J=3.6 Hz, 1H), 5.47-5.34 (m, 1H), 4.66 (dd, J=8.4, 3.9 Hz, 1H), 3.89-3.73 (m, 2H), 2.67-2.54 (m, 1H), 2.50-2.36 (m, 1H), 2.35-2.27 (m, 3H), 2.13-2.01 (m, 1H), 0.94 (s, 9H) and 0.14 (d, J=2.4 Hz, 6H)) was prepared as described in Example 4 above utilizing (4,6-dichloropyrimidin-5-yl)acetaldehyde prepared as described in Example 2.

7-[(1R,3S,4S)-3-{[tert-butyl(dimethyl)silyl]oxy}-4-({[tert-butyl(dimethyl)silyl]oxy}methyl)cyclopentyl]-4-chloro-2-ethyl-7H-pyrrolo[2,3-d]pyrimidine (¹H NMR (300 MHz, CDCl₃) δ 7.18 (d, J=3.6 Hz, 1H), 6.52 (d, J=3.6 Hz, 1H), 5.43 (d, J=4.7 Hz, 1H), 4.50 (s, 1H), 3.78 (dd, J=10.0, 7.2 Hz, 1H), 3.63 (dd, J=10.0, 6.7 Hz, 1H), 3.01 (q, J=7.5 Hz, 2H), 2.53 (s, 1H), 2.38-2.08 (m, 4H), 2.07-1.89 (m, 1H), 1.45-1.34 (m, 3H), 0.93 (s, 9H), 0.90 (s, 9H), 0.09 (d, J=1.8 Hz, 6H) and 0.07 (s, 6H)) was prepared as described in Example 4 Step 1 above utilizing (4,6-dichloro-2-ethylpyrimidin-5-yl)acetaldehyde prepared as described in Example 2.

Example 5

Synthesis of 2-(4,4,5,5-tetramethyl-1,3,2-dioxaborolan-2-yl)-1H-indole

An argon-purged, round-bottom flask was charged with dip-methoxobis(1,5-cyclooctadiene)diiridium(I) (64 mg, 0.096 mmol) and 4,4'-di-tert-butyl-2,2'-bipyridine (52 mg, 0.19 mmol). The flask was evacuated and backfilled with argon. Indole (1.50 g, 12.8 mmol) and bis(pinacolato)diboron (1.62 g, 6.40 mmol) were added and the flask was again purged with argon. Dry hexane (38.5 mL) was then introduced and the mixture was stirred at room temperature under argon for 8 h. The reaction mixture was concentrated under reduced pressure and the resulting residue was purified by column chromatography (SiO₂, 0-10% EtOAc/hexanes) to give the title compound (2.66 g, 85% yield). 1H NMR (300 MHz, d₆-DMSO) δ 11.27 (s, 1H), 7.55 (d, J=7.9 Hz, 1H), 7.38 (dd, J=8.2, 0.8 Hz, 1H), 7.15-7.06 (m, 1H), 7.00-6.92 (m, 1H), 6.90-6.87 (m, 1H) and 1.32 (s, 12H).

The following indole boronates were prepared in an analogous manner using the appropriate indole starting materials:

Example 6

Synthesis of [(1 S,2S,4R)-2-{[tert-butyl(dimethyl)silyl]oxy}-4-{4-[6-(trifluoromethyl)-1H-indol-2-yl]-7H-pyrrolo[2,3-d]pyrimidin-7-yl}cyclopentyl]methanol

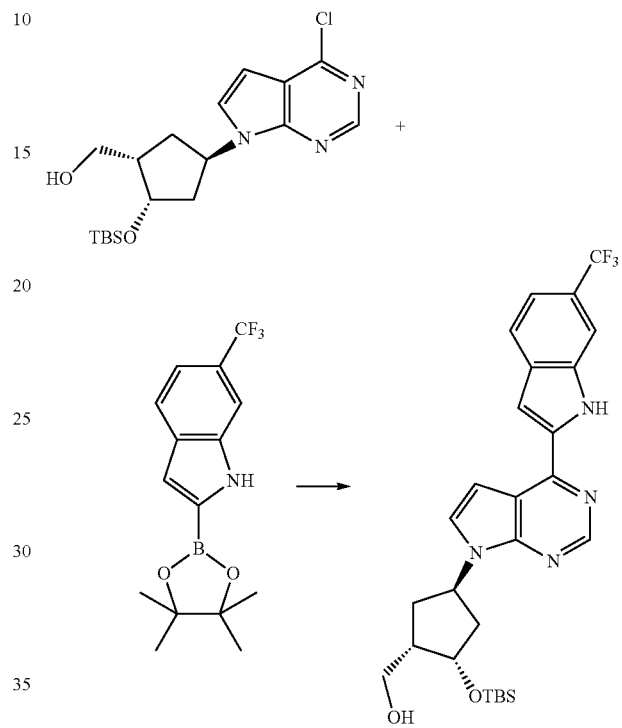

A mixture of [(1S,2S,4R)-2-{[tert-butyl(dimethyl)silyl]oxy}-4-(4-chloro-7H-pyrrolo[2,3-d]pyrimidin-7-yl)cyclopentyl]methanol (0.160 g, 0.419), 2-(4,4,5,5-tetramethyl-1,3,2-dioxaborolan-2-yl)-6-(trifluoromethyl)-1H-indole (0.260 g, 0.836 mmol) and cesium carbonate (0.409 g, 1.26 mmol) in 1,4-dioxane (3.00 mL, 38.4 mmol) and water (0.600 mL, 33.3 mmol) was degassed for 5 min by bubbling argon through the reaction mixture. Tetrakis(triphenylphosphine)palladium (0.0484 g, 0.0419 mmol) was added and the reaction vessel was sealed. The reaction mixture was heated in a microwave at 150° C. for 30 min. The mixture was diluted with EtOAc and water. The aqueous phase was extracted with EtOAc (2×). The combined organic phases were washed with brine, dried over Na₂SO₄, filtered and concentrated under reduced pressure. Purification by column chromatography (SiO₂, elution with 0-10% MeOH in DCM)

| Starting Indole | Indole Boronate Prepared | Characterizing data |
|---|---|---|
| 6-chloro-5-fluoro-1H-indole | 6-chloro-5-fluoro-2-(4,4,5,5-tetramethyl-1,3,2-dioxaborolan-2-yl)-1H-indole | ¹H NMR (400 MHz, CDCl₃) δ 7.43-7.34 (m, 2H), 7.03 (dd, J = 2.0, 0.9 Hz, 1H) and 1.36 (s, 12H). |
| tert-butyl 3-methyl-1H-indole-1-carboxylate | tert-butyl 3-methyl-2-(4,4,5,5-tetramethyl-1,3,2-dioxaborolan-2-yl)-1H-indole-1-carboxylate | ¹H NMR (300 MHz, CDCl₃) δ 7.85 (d, J = 7.7 Hz, 1H), 7.50-7.43 (m, 1H), 7.29-7.14 (m, 2H), 2.31 (s, 3H), 1.67 (s, 9H) and 1.42 (s, 12H). |
| 6-(trifluoromethyl)-1H-indole | 2-(4,4,5,5-tetramethyl-1,3,2-dioxaborolan-2-yl)-6-(trifluoromethyl)-1H-indole | LC/MS: (M + H) 312 | provided the title compound as a yellow oil (211 mg, 95%). $^1$H NMR (300 MHz, CD$_3$OD) 8.82 (s, 1H), 7.83 (d, J=8.8 Hz, 2H), 7.72-7.52 (m, 2H), 7.50 (s, 1H), 7.30 (d, J=8.5 Hz, 1H), 7.10 (d, J=3.7 Hz, 1H), 5.58 (td, J=13.4, 8.5 Hz, 1H), 4.59 (s, 1H), 3.79 (dd, J=10.3, 7.1 Hz, 1H), 3.67-3.55 (m, 1H), 2.62 (dd, J=10.1, 6.3 Hz, 1H), 2.25 (ddd, J=19.8, 13.0, 9.5 Hz, 3H), 2.05 (ddd, J=13.8, 9.1, 5.0 Hz, 1H), 0.97 (s, 9H) and 0.14 (d, J=2.0 Hz, 6H).

Example 6a

Synthesis of {(1S,2S,4R)-2-hydroxy-4-[4-(5-methoxy-1H-indol-2-yl)-7H-pyrrolo[2,3-d]pyrimidin-7-yl]cyclopentyl}methyl sulfamate (I-03)

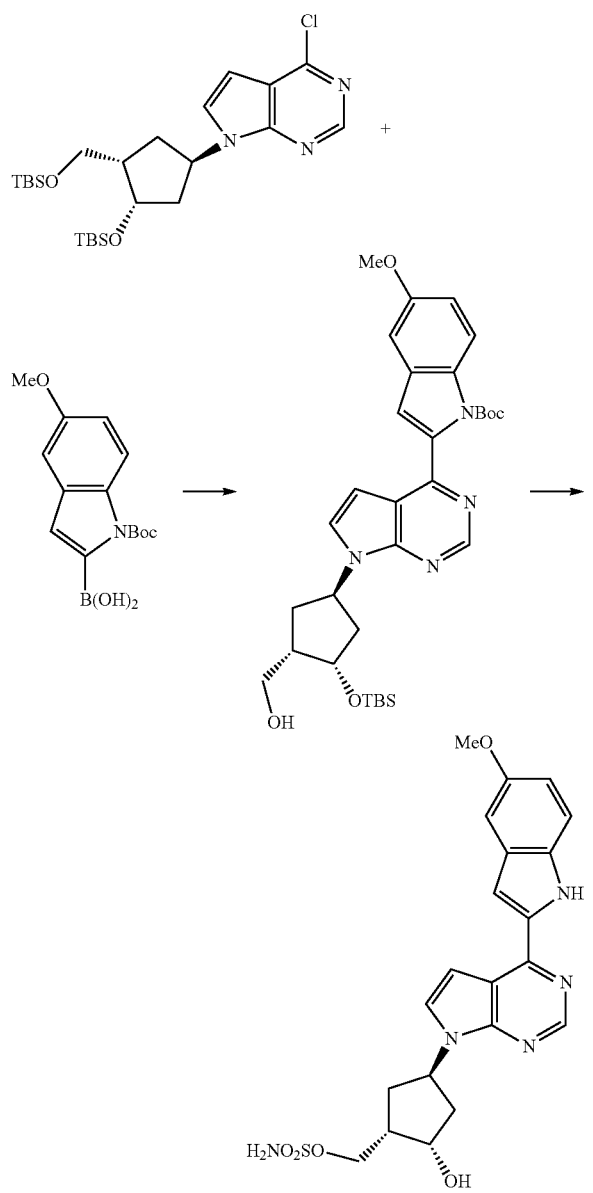

Step 1: tert-butyl 2-(7-[(1R,3S,4S)-3-{[tert-butyl(dimethyl)silyl]oxy}-4-({[tert-butyl(dimethyl)silyl]oxy)methyl)cyclopentyl]-7H-pyrrolo[2,3-d]pyrimidin-4-yl}-5-methoxy-1H-indole-1-carboxylate A mixture of 7-[(1R,3S,4S)-3-{[tert-butyl(dimethyl)silyl]oxy}-4-({[tert-butyl(dimethyl)silyl]-oxy}methyl)cyclopentyl]-4-chloro-7H-pyrrolo[2,3-d]pyrimidine (0.200 g, 0.403 mmol), 1-(tert-Butoxycarbonyl)-5-methoxy-1H-indol-2-yl-boronic acid (0.176 g, 0.604 mmol) and cesium carbonate (0.394 g, 1.21 mmol) in 1,4-dioxane (3.0 mL) and water (0.600 mL) was degassed for 5 min by bubbling argon through the reaction mixture. Tetrakis(triphenylphosphine)palladium(0) (0.0466 g, 0.0403 mmol) was added and the vessel was sealed and heated in a microwave for 30 min at 150° C. The reaction mixture was diluted with EtOAc and water. The aqueous phase was extracted with EtOAc (2×), dried over Na$_2$SO$_4$, filtered and concentrated under reduced pressure. Purification by column chromatography (SiO$_2$, elution with 0-20% EtOAc/hexanes) provided tert-butyl 2-{7-[1R,3S,4S)-3-{[tert-butyl(dimethyl)silyl]oxy}-4-({[tert-butyl(dimethyl)silyl]oxy}methyl)cyclopentyl]-7H-pyrrolo[2,3-d]pyrimidin-4-yl}-5-methoxy-1H-indole-1-carboxylate as a pale yellow solid (183 mg, 64%). $^1$H NMR (300 MHz, CDCl$_3$) δ 8.91 (s, 1H), 8.13 (d, J=9.0 Hz, 1H), 7.29 (d, J=3.7 Hz, 1H), 7.08 (d, J=2.5 Hz, 1H), 7.02 (dd, J=9.0, 2.6 Hz, 1H), 6.94 (s, 1H), 6.58 (d, J=3.6 Hz, 1H), 5.54 (td, J=12.9, 8.7 Hz, 1H), 4.51 (s, 1H), 3.92-3.56 (m, 5H), 2.63-2.43 (m, 1H), 2.41-2.09 (m, 3H), 1.98 (ddd, J=13.6, 8.9, 4.6 Hz, 1H), 1.19 (s, 9H), 0.98-0.91 (m, 9H), 0.91 (s, 9H), 0.10 (t, J=3.6 Hz, 6H) and 0.07 (s, 6H).

Step 2: tert-butyl 2-{7-[(1R,3S,4S)-3-{[tert-butyl(dimethyl)silyl]oxy}-4-(hydroxymethyl)cyclopentyl]-7H-pyrrolo[2,3-d]pyrimidin-4-yl}-5-methoxy-1H-indole-1-carboxylate Mono-deprotection of tert-butyl 2-{7-[(1R,3S,4S)-3-{[tert-butyl(dimethyl)silyl]oxy}-4-({[tert-butyl(dimethyl)silyl]oxy}methyl)cyclopentyl]-7H-pyrrolo[2,3-d]pyrimidin-4-yl}-5-methoxy-1H-indole-1-carboxylate as described in Step 2 of Example 4 provided tert-butyl 2-{7-[(1R,3S,4S)-3-{[tert-butyl(dimethyl)silyl]oxy}-4-(hydroxymethyl)cyclopentyl]-7H-pyrrolo[2, 3-d]pyrimidin-4-yl}-5-methoxy-1H-indole-1-carboxylate. $^1$H NMR (300 MHz, CD$_3$OD) δ 8.78 (s, 1H), 8.10 (d, J=9.1 Hz, 1H), 7.68 (d, J=3.7 Hz, 1H), 7.18 (d, J=2.4 Hz, 1H), 7.03 (dd, J=9.1, 2.6 Hz, 1H), 6.98 (s, 1H), 6.63 (d, J=3.7 Hz, 1H), 5.57 (dd, J=9.3, 5.0 Hz, 1H), 4.59 (d, J=3.3 Hz, 1H), 3.86 (s, 3H), 3.79 (dd, J=10.3, 7.1 Hz, 1H), 3.62 (dd, J=10.3, 6.9 Hz, 1H), 2.63 (s, 1H), 2.26 (ddd, J=23.7, 14.0, 6.2 Hz, 3H), 2.14-1.94 (m, 1H), 1.14 (s, 9H), 0.97 (s, 9H) and 0.14 (d, J=1.9 Hz, 6H).

Step 3: tert-butyl 2-(7-{(1R,3S,4S)-3-hydroxy-4-[(sulfamoyloxy)methyl]cyclopentyl}-7H-pyrrolo[2,3-d]pyrimidin-4-yl)-5-methoxy-1H-indole-1-carboxylate Tert-butyl 2-{7-[(1R,3S,4S)-3-{[tert-butyl(dimethyl)silyl]oxy}-4-(hydroxymethyl)cyclopentyl]-7H-pyrrolo[2,3-d]

pyrimidin-4-yl}-5-methoxy-1H-indole-1-carboxylate (0.100 g, 0.169 mmol) was dissolved in DMF (1.11 mL, 14.34 mmol). Chlorosulfonamide (29.2 mg, 0.253 mmol) was added to the reaction mixture which was stirred at room temperature for 2 h. Hydrochloric acid (6.0 M in water, 0.28 mL, 1.69 mmol) was added and the reaction mixture was stirred at room temperature for 3 h. The reaction mixture was quenched with sodium carbonate (178.8 mg, 1.687 mmol), diluted with EtOAc and MeOH, and filtered. The filtrate was concentrated and purified by column chromatography (SiO$_2$, elution with 0-5% MeOH/DCM) to give tert-butyl 2-(7-{(1R,3S,4S)-3-hydroxy-4-[(sulfamoyloxy)methyl]cyclopentyl}-7H-pyrrolo[2,3-d]pyrimidin-4-yl)-5-methoxy-1H-indole-1-carboxylate (67 mg, 71%) LCMS: (M+H):558.

Step 4: {(1S,2S,4R)-2-hydroxy-4-[4-(5-methoxy-1H-indol-2-yl)-7H-pyrrolo[2,3-d]pyrimidin-7-yl]cyclopentyl}methyl sulfamate Tert-butyl 2-[7-((1R,3S,4S)-3-{[(aminosulfonyl)oxy]methyl}-4-hydroxycyclopentyl)-7H-pyrrolo[2,3-d]pyrimidin-4-yl]-5-methoxy-1H-indole-1-carboxylate (0.067 g, 0.12 mmol) was dissolved into methanol (1.00 mL). Potassium carbonate (0.0830 g, 0.601 mmol) and water (1.00 mL) were added and the reaction mixture was heated at 100° C. for 4 h. The reaction mixture was cooled to room temperature and diluted with EtOAc and water. The aqueous phase was extracted with EtOAc (2×) and the combined organic phases were concentrated under reduced pressure. Purification by column chromatography (SiO$_2$, elution with 20-50% EtOAc/DCM and then 2-5% MeOH/DCM) provided {(1S,2S,4R)-2-hydroxy-4-[4-(5-methoxy-1H-indol-2-yl)-7H-pyrrolo[2,3-d]pyrimidin-7-yl]cyclopentyl}methyl sulfamate (22 mg, 71%).

$^1$H NMR (300 MHz, CD$_3$OD) δ 8.75 (s, 1H), 7.64 (d, J=3.7 Hz, 1H), 7.39 (d, J=8.9 Hz, 1H), 7.35 (s, 1H), 7.15 (d, J=2.4 Hz, 1H), 7.07 (d, J=3.7 Hz, 1H), 6.89 (dd, J=8.9, 2.4 Hz, 1H), 5.60 (dt, J=13.8, 8.8 Hz, 1H), 4.53 (d, J=3.5 Hz, 1H), 4.39 (dd, J=9.7, 7.6 Hz, 1H), 4.22 (dd, J=9.8, 7.3 Hz, 1H), 3.84 (s, 3H), 2.92 (t, J=10.4 Hz, 1H) and 2.43-2.05 (m, 4H).

Example 6b

The following compounds were prepared as described in Examples 6a using the appropriate protected boronic acid.

| Cpd No. | Name | Starting protected boronic acid | NMR data |
| --- | --- | --- | --- |
| I-11 | {(1S,2S,4R)-4-[4-(5-fluoro-1H-indol-2-yl)-7H-pyrrolo[2,3-d]pyrimidin-7-yl]-2-hydroxycyclopentyl}methyl sulfamate | [1-(tert-butoxycarbonyl)-5-fluoro-1H-indol-2-yl]boronic acid | $^1$H NMR (400 MHz, CD$_3$OD) δ 8.78 (s, 1H), 7.67 (d, J = 3.7 Hz, 1H), 7.47 (dd, J = 8.9, 4.5 Hz, 1H), 7.40 (s, 1H), 7.33 (dd, J = 9.6, 2.4 Hz, 1H), 7.08 (d, J = 3.7 Hz, 1H), 7.00 (td, J = 9.2, 2.5 Hz, 1H), 5.61 (dt, J = 13.1, 8.5 Hz, 1H), 4.53 (d, J = 3.6 Hz, 1H), 4.39 (dd, J = 9.7, 7.6 Hz, 1H), 4.22 (dd, J = 9.7, 7.3 Hz, 1H), 2.90 (d, J = 4.0 Hz, 1H), 2.41-2.20 (m, 3H) and 2.13 (ddd, J = 14.0, 9.2, 5.1 Hz, 1H). |
| I-12 | {(1S,2S,4R)-2-hydroxy-4-[4-(7-methoxy-1H-indol-2-yl)-7H-pyrrolo[2,3-d]pyrimidin-7-yl]cyclopentyl}methyl sulfamate | [1-(tert-butoxycarbonyl)-7-methoxy-1H-indol-2-yl]boronic acid | $^1$H NMR (400 MHz, CD$_3$OD) δ 8.77 (s, 1H), 7.65 (d, J = 3.7 Hz, 1H), 7.41 (s, 1H), 7.27 (d, J = 8.0 Hz, 1H), 7.07 (d, J = 3.7 Hz, 1H), 7.01 (t, J = 7.9 Hz, 1H), 6.75 (d, J = 7.6 Hz, 1H), 5.61 (dt, J = 13.3, 8.6 Hz, 1H), 4.53 (d, J = 3.2 Hz, 1H), 4.39 (dd, J = 9.7, 7.6 Hz, 1H), 4.22 (dd, J = 9.8, 7.3 Hz, 1H), 4.01 (s, 3H), 2.90 (d, J = 4.5 Hz, 1H), 2.42-2.20 (m, 3H) and 2.13 (ddd, J = 14.0, 9.3, 5.0 Hz, 1H). |
| I-13 | {(1S,2S,4R)-2-hydroxy-4-[4-(3-methyl-1H-indol-2-yl)-7H-pyrrolo[2,3-d]pyrimidin-7-yl]cyclopentyl}methyl sulfamate | [1-(tert-butoxycarbonyl)-3-methyl-1H-indol-2-yl]boronic acid | $^1$H NMR (400 MHz, CD$_3$OD) δ 8.80 (s, 1H), 7.64 (t, J = 6.6 Hz, 2H), 7.45 (d, J = 8.2 Hz, 1H), 7.22 (t, J = 7.6 Hz, 1H), 7.08 (t, J = 7.5 Hz, 1H), 6.84 (d, J = 3.7 Hz, 1H), 5.63 (td, J = 13.4, 8.6 Hz, 1H), 4.53 (d, J = 3.0 Hz, 1H), 4.39 (dd, J = 9.7, 7.6 Hz, 1H), 4.22 (dd, J = 9.7, 7.4 Hz, 1H), 3.00-2.82 (m, 1 H), 2.58 (s, 3H), 2.45-2.20 (m, 3H) and 2.14 (ddd, J = 14.1, 9.3, 5.0 Hz, 1H). |
| I-04 | {(1S,2S,4R)-4-[4-(6-chloro-1H-indol-2-yl)-7H-pyrrolo[2,3-d]pyrimidin-7-yl]-2-hydroxycyclopentyl}methyl sulfamate | [1-(tert-butoxycarbonyl)-6-chloro-1H-indol-2-yl]boronic acid | $^1$H NMR (300 MHz, CD$_3$OD) δ 8.78 (s, 1H), 7.65 (dd, J = 8.8, 6.1 Hz, 2H), 7.52 (d, J = 1.0 Hz, 1H), 7.42 (s, 1H), 7.12-6.98 (m, 2H), 5.61 (td, J = 13.7, 8.8 Hz, 1H), 4.53 (d, J = 3.4 Hz, 1H), 4.39 (dd, J = 9.7, 7.6 Hz, 1H), 4.22 (dd, J = 9.7, 7.3 Hz, 1H), 2.90 (q, J = 17.0 Hz, 1H) and 2.43-2.06 (m, 4H). |

-continued

| Cpd No. | Name | Starting protected boronic acid | NMR data |
|---|---|---|---|
| I-05 | {(1S,2S,4R)-4-[4-(6-cyano-1H-indol-2-yl)-7H-pyrrolo[2,3-d]pyrimidin-7-yl]-2-hydroxycyclopentyl}methyl sulfamate | [1-(tert-butoxycarbonyl)-6-cyano-1H-indol-2-yl]boronic acid | $^1$H NMR (400 MHz, $d_6$-DMSO) δ 12.44 (s, 1H), 8.90 (s, 1H), 7.98 (d, J = 3.7 Hz, 1H), 7.94 (s, 1H), 7.84 (d, J = 8.3 Hz, 1H), 7.70 (s, 1H), 7.44 (s, 1H), 7.39 (dd, J = 8.3, 1.4 Hz, 1H), 7.22 (d, J = 3.7 Hz, 1H), 5.56 (dd, J = 14.2, 8.8 Hz, 1H), 4.37 (s, 1H), 4.25 (dd, J = 9.7, 7.0 Hz, 1H), 4.12-4.02 (m, 1H), 2.79 (d, J = 3.9 Hz, 1H), 2.21 (dtd, J = 19.2, 13.3, 6.9 Hz, 3H) and 2.03 (ddd, J = 19.1, 9.5, 4.8 Hz, 1H). |

Example 7

Synthesis of {(1S,2S,4R)-2-{[tert-butyl(dimethyl)silyl]oxy}-4-[4-(1H-indol-2-yl)-7H-pyrrolo[2,3-d]pyrimidin-7-yl]cyclopentyl}methyl sulfamate

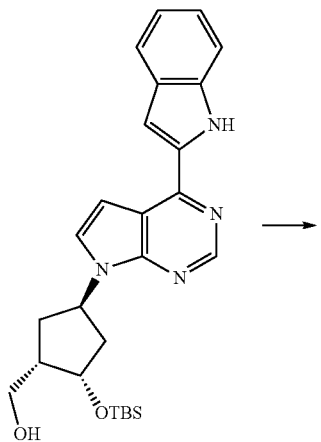

{(1S,2S,4R)-2-{[tert-butyl(dimethyl)silyl]oxy}-4-[4-(1H-indol-2-yl)-7H-pyrrolo[2,3-d]pyrimidin-7-yl]cyclopentyl}methanol (1.00 g, 2.16 mmol) was dissolved in DMF (16.74 mL) and chlorosulfonamide (0.3746 g, 3.242 mmol) was added. The reaction solution was stirred at room temperature for 90 min. The reaction solution was diluted with ethyl acetate (150 mL) and washed with half-saturated sodium bicarbonate solution (200 mL). The aqueous phase was extracted with additional ethyl acetate (2×75 mL). The extracts were combined, washed with saturated aq. sodium bicarbonate solution, water and brine then dried over sodium sulfate, filtered and concentrated under reduced pressure. The crude residue was purified by column chromatography (SiO$_2$, 10-50% EtOAc/hexanes) to give the title compound (831 mg, 71%). $^1$H NMR (300 MHz, CDCl$_3$) δ 9.79 (s, 1H), 8.83 (s, 1H), 7.73 (d, J=8.0 Hz, 1H), 7.48 (d, J=8.2 Hz, 1H), 7.37 (d, J=1.2 Hz, 1H), 7.35-7.28 (m, 2H), 7.15 (t, J=7.5 Hz, 1H), 6.94 (t, J=7.0 Hz, 1H), 5.49 (td, J=13.6, 8.7 Hz, 1H), 4.80 (s, 2H), 4.57 (d, J=2.2 Hz, 1H), 4.47-4.35 (m, 1H), 4.29 (dd, J=9.5, 6.6 Hz, 1H), 2.89 (d, J=17.6 Hz, 1H), 2.31 (ddd, J=19.8, 11.5, 6.6 Hz, 3H), 2.14 (ddd, J=13.7, 9.1, 4.8 Hz, 1H), 0.95 (s, 9H) and 0.14 (s, 6H).

Example 8

Synthesis of {(1S,2S,4R)-2-hydroxy-4-[4-(1H-indol-2-yl)-7H-pyrrolo[2,3-d]pyrimidin-7-yl]cyclopentyl}methyl sulfamate hydrochloride (I-01)

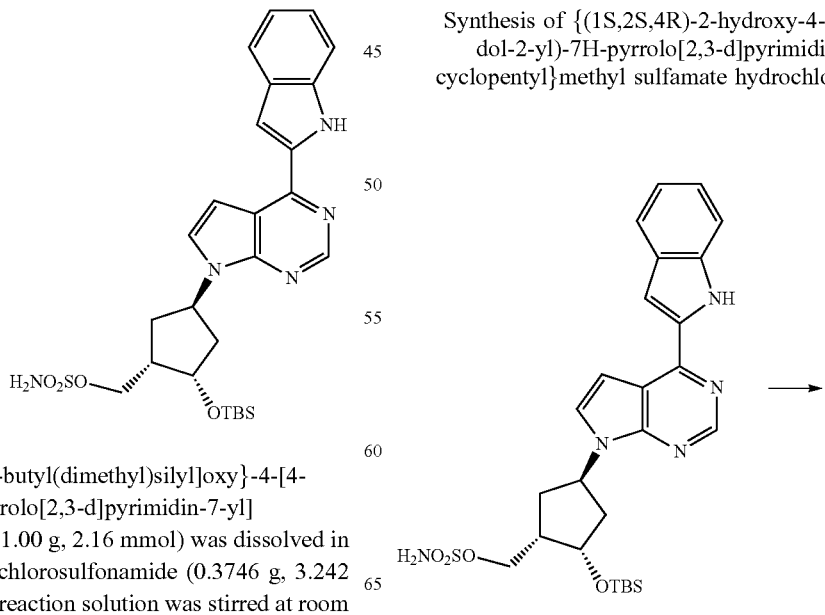

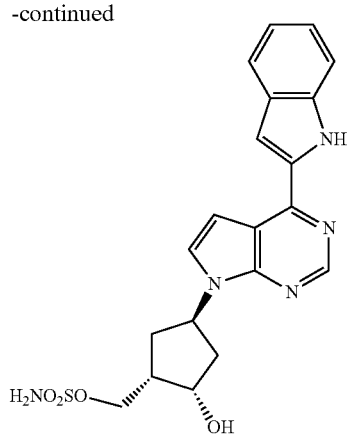

Step 1: {(1S,2S,4R)-2-hydroxy-4-[4-(1H-indol-2-yl)-7H-pyrrolo[2,3-d]pyrimidin-7-yl]cyclopentyl}methyl sulfamate (I-01)

{(1S,2S,4R)-2-{[tert-butyl(dimethyl)silyl]oxy}-4-[4-(1H-indol-2-yl)-7H-pyrrolo[2,3-d]pyrimidin-7-yl]cyclopentyl}methyl sulfamate (8.88 g, 16.4 mmol) was dissolved in DMF (140 mL). Hydrochloric acid (6.0 M in water, 54.6 mL, 328 mmol) was added over 5 min by pipet. The reaction mixture turned red-yellow, and a slight exotherm was observed as a flaky yellow precipitate formed on acidification. After 2 h, a thick yellow precipitate formed. The reaction mixture was transferred to a 2 L separatory funnel containing saturated aqueous sodium bicarbonate solution (350 mL), water (350 mL) and ethyl acetate (500 mL). The mixture was shaken, and the phases were separated. The aqueous phase was extracted with additional ethyl acetate (2×500 mL). The extracts were combined, washed with saturated aqueous sodium bicarbonate solution, water and brine then dried over sodium sulfate, filtered and concentrated under reduced pressure. The crude product was isolated as a thick yellow oil which was dried under high vacuum. The oil was then treated with 100 mL ether. The product separated as a thick yellow oil, yielding no solid. The mixture was concentrated under reduced pressure and dried in vacuo. Methylene chloride was added (25 mL). A solid block quickly formed on sonication. Ether was added (50 mL) and the mixture formed a filterable solid. The solids were isolated by suction filtration and the product was washed with ether (100 mL) and dried under suction to give the title compound as a pale yellow solid (5.51 g, 79%). $^1$H NMR (300 MHz, d$_6$-DMSO) δ 11.88 (s, 1H), 8.83 (s, 1H), 7.90 (d, J=3.7 Hz, 1H), 7.66 (d, J=7.9 Hz, 1H), 7.53 (d, J=7.7 Hz, 2H), 7.42 (s, 2H), 7.25-7.13 (m, 2H), 7.05 (t, J=7.3 Hz, 1H), 5.64-5.46 (m, 1H), 4.98 (s, 1H), 4.37 (s, 1H), 4.26 (dd, J=9.7, 7.1 Hz, 1H), 4.15-3.97 (m, 1H), 2.79 (d, J=4.2 Hz, 1H) and 2.34-1.92 (m, 4H).

Step 2: {(1S,2S,4R)-2-hydroxy-4-[4-(1H-indol-2-yl)-7H-pyrrolo[2,3-d]pyrimidin-7-yl]cyclopentyl}methyl sulfamate hydrochloride (I-01.HCl)

{(1S,2S,4R)-2-hydroxy-4-[4-(1H-indol-2-yl)-7H-pyrrolo[2,3-d]pyrimidin-7-yl]cyclopentyl}methyl sulfamate (11.63 g, 27.20 mmol) was suspended in absolute ethanol (1.0 L). A solution of HCl in ethanol (1.25 M, 32.6 mL, 40.8 mmol) was added. The yellow suspension was stirred at room temperature for 30 minutes and concentrated under reduced pressure to ½ volume. The precipitate was isolated by filtration and dried in vacuo to provide a yellow solid cake. Filtrate was retained and concentrated to dryness. The resulting solids were suspended in ethanol (25 mL), filtered and washed with ethanol (2×10 mL). The combined powders were dried in vacuo at 40° C. to give the title compound as the HCl salt (12.12 g). $^1$H NMR (300 MHz, d$_6$-DMSO) δ 12.03 (s, 1H), 8.91 (s, 1H), 8.02 (d, J=3.7 Hz, 1H), 7.74-7.63 (m, 2H), 7.57 (d, J=8.2 Hz, 1H), 7.45 (s, 2H), 7.31 (d, J=3.7 Hz, 1H), 7.28-7.21 (m, 1H), 7.08 (dd, J=11.0, 4.0 Hz, 1H), 5.58 (dt, J=14.5, 8.9 Hz, 2H), 4.38 (s, 1H), 4.27 (dd, J=9.7, 7.0 Hz, 1H), 4.08 (dd, J=9.6, 8.0 Hz, 1H), 2.90-2.68 (m, 1H) and 2.37-1.96 (m, 4H).

Example 8a

The following compounds were prepared as described in Examples 6 and 7, Step 1 of Example 8 and Step 4 of Example 6a using the appropriate boronates and chloropyrimidines:

| Cpd No. | Name | Starting boronate | Starting chloropyrimidine | NMR data |
|---|---|---|---|---|
| I-06 | {(1S,2S,4R)-2-hydroxy-4-[4-(6-methyl-1H-indol-2-yl)-7H-pyrrolo[2,3-d]pyrimidin-7-yl]cyclopentyl}methyl sulfamate | tert-butyl 6-methyl-2-(4,4,5,5-tetramethyl-1,3,2-dioxaborolan-2-yl)-1H-indole-1-carboxylate | [(1S,2S,4R)-2-{[tert-butyl(dimethyl)silyl]oxy}-4-(4-chloro-7H-pyrrolo[2,3-d]pyrimidin-7-yl)cyclopentyl]methanol | $^1$H NMR (400 MHz, CD$_3$OD) δ 8.74 (s, 1H), 7.63 (d, J = 3.6 Hz, 1H), 7.54 (d, J = 8.1 Hz, 1H), 7.37 (s, 1H), 7.30 (s, 1H), 7.07 (d, J = 3.7 Hz, 1H), 6.92 (d, J = 8.2 Hz, 1H), 5.67-5.51 (m, 1H), 4.53 (s. 1H), 4.39 (dd, J = 9.7, 7.6 Hz, 1H), 4.22 (dd, J = 9.5, 7.1 Hz, 1H), 2.90 (s, 1H), 2.45 (s, 3H), 2.40-2.21 (m, 3H) and 2.19-2.06 (m, 1H). |
| I-07 | {(1S,2S,4R)-2-hydroxy-4-[4-(6-methoxy-1H-indol-2-yl)-7H-pyrrolo[2,3-d]pyrimidin-7-yl]cyclopentyl}methyl | tert-butyl 6-methoxy-2-(4,4,5,5-tetramethyl-1,3,2-dioxaborolan-2-yl)-1H-indole-1- | [(1S,2S,4R)-2-{[tert-butyl(dimethyl)silyl]oxy}-4-(4-chloro-7H-pyrrolo[2,3-d]pyrimidin- | $^1$H NMR (400 MHz, CD$_3$OD) δ 8.72 (s, 1H), 7.61 (d, J = 3.7 Hz, 1H), 7.53 (d, J = 8.8 Hz, 1H), 7.36 (s, 1H), 7.03 (dd, J = 14.2, 2.8 Hz, 2H), 6.73 (dd, J = 8.7, 2.2 Hz, 1H), 5.67-5.53 (m, 1H), 4.53 (s, 1H), 4.39 (dd, J = 9.7, 7.6 Hz, 1H), 4.22 (dd, |

-continued

| Cpd No. | Name | Starting boronate | Starting chloropyrimidine | NMR data |
|---|---|---|---|---|
| | sulfamate | carboxylate | 7-yl)cyclopentyl]methanol | J = 9.7, 7.4 Hz, 1H), 3.85 (s, 3H), 2.89 (d, J = 4.2 Hz, 1H), 2.43-2.20 (m, 3H) and 2.12 (ddd, J = 13.8, 9.1, 4.8 Hz, 1H). |
| I-09 | {(1S,2S,4RH-[4-(6-chloro-5-fluoro-1H-indol-2-yl)-7H-pyrrolo[2,3-d]pyrimidin-7-yl]-2-hydroxycyclopentyl}methyl sulfamate | tert-butyl 6-chloro-5-fluoro-2-(4,4,5,5-tetramethyl-1,3,2-dioxaborolan-2-yl)-1H-indole-1-carboxylate | [(1S,2S,4R)-2-{[tert-butyl(dimethyl)silyl]oxy}-4-(4-chloro-7H-pyrrolo[2,3-d]pyrimidin-7-yl)cyclopentyl]methanol | $^1$H NMR (400 MHz, CD$_3$OD) δ 8.78 (s, 1H), 7.67 (d, J = 3.7 Hz, 1H), 7.58 (d, J = 6.4 Hz, 1H), 7.48 (d, J = 9.8 Hz, 1H), 7.40 (s, 1H), 7.06 (d, J = 3.7 Hz, 1H), 5.66-5.55 (m, 1H), 4.53 (d, J = 3.1 Hz, 1H), 4.39 (dd, J = 9.7, 7.6 Hz, 1H), 4.22 (dd, J = 9.8, 7.3 Hz, 1H), 2.90 (d, J = 4.5 Hz, 1H), 2.43-2.22 (m, 3H) and 2.13 (ddd, J = 14.3, 9.5, 5.0 Hz, 1H). |

Example 8b

The following compound was prepared as described in Examples 6 and 7, Step 1 of Example 8, Step 4 of Example 6a using the appropriate boronate and chloropyrimidine:

| Cpd No. | Name | Starting boronate | Starting chloropyrimidine | NMR data |
|---|---|---|---|---|
| I-08 | {(1S,2S,4R)-2-hydroxy-4-[4-(1H-indol-2-yl)-2-methyl-7H-pyrrolo[2,3-d]pyrimidin-7-yl]cyclopentyl}methyl sulfamate | tert-butyl 2-(4,4,5,5-tetramethyl-1,3,2-dioxaborolan-2-yl)-1H-indole-1-carboxylate | [(1S,2S,4R)-2-{[tert-butyl(dimethyl)silyl]oxy}-4-(4-chloro-2-methyl-7H-pyrrolo[2,3-d]pyrimidin-7-yl)cyclopentyl]methanol | $^1$H NMR (300 MHz, d$_6$-DMSO) δ 11.65 (s, 1H), 7.78 (d, J = 3.6 Hz, 1H), 7.64 (d, J = 7.9 Hz, 1H), 7.57 (d, J = 8.1 Hz, 1H), 7.49 (s, 1H), 7.42 (s, 2H), 7.19 (dd, J = 8.1, 7.1 Hz, 1H), 7.09 (d, J = 3.7 Hz, 1H), 7.04 (t, J = 7.5 Hz, 1H), 5.64-5.46 (m, 1 H), 4.97 (s, 1H), 4.36 (8, 1H), 4.25 (dd, J = 9.6, 7.1 Hz, 1H), 4.07 (t, J = 8.8 Hz, 1H), 2.75 (s, 4H), 2.28-1.88 (m, 4H). |

The HCl salt of {(1S,2S,4R)-2-hydroxy-4-[4-(1H-indol-2-yl)-2-methyl-7H-pyrrolo[2,3-d]pyrimidin-7-yl]cyclopentyl}methyl sulfamate (I-08.HCl) was prepared as described in Step 2 of Example 8 using the {(1 S,2S,4R)-2-hydroxy-4-[4-(1H-indol-2-yl)-2-methyl-7H-pyrrolo[2,3-d]pyrimidin-7-yl]cyclopentyl}methyl sulfamate and HCl:

| Cpd No. | Name | NMR data |
|---|---|---|
| I-08•HCl | {(1S,2S,4R)-2-hydroxy-4-[4-(1H-indol-2-yl)-2-methyl-7H-pyrrolo[2,3-d]pyrimidin-7-yl]cyclopent- yl}methyl sulfamate HCl salt | $^1$H NMR (300 MHz, d$_6$-DMSO) δ 12.48 (s, 1H), 8.08 (d, J = 3.6 Hz, 1H), 7.84 (s, 1H), 7.73 (d, J = 8.0 Hz, 1H), 7.59 (d, J = 8.3 Hz, 1H), 7.51-7.37 (m, 3H), 7.31 (dd, J = 11.3, 4.0 Hz, 1H), 7.13 (t, J = 7.5 Hz, 1H), 5.75-5.41 (m, 2H), 4.37 (d, J = 3.5 Hz, 1H), 4.26 (dd, J = 9.7, 7.0 Hz, 1H), 4.07 (dd, J = 9.6, 8.0 Hz, 1H), 2.85-2.72 (m, 1H), 2.30-2.08 (m, 3H) and 2.08-1.87 (m, 1H). |

Example 8c

The following compounds were prepared as described in Examples 6 and 7 and Step 1 of Example 8 using the appropriate boronates and chloropyrimidines:

| Cpd No. | Name | Starting boronate | Starting chloropyrimidine | NMR data |
|---|---|---|---|---|
| I-10 | tert-butyl 2-(7-{(1R,3S,4S)-3-hydroxy-4-[(sulfamoyloxy)methyl]cyclo- | tert-butyl 6-methyl-2-(4,4,5,5-tetramethyl-1,3,2-dioxaborolan-2-yl)- | [(1S,2S,4R)-2-{[tert-butyl(dimethyl)silyl]oxy}-4-(4-chloro-7H- | $^1$H NMR (400 MHz, CDCl$_3$) δ 8.87 (d, J = 8.2 Hz, 1H), 7.76 (d, J = 2.2 Hz, 1H), 7.50 (t, J = 9.1 Hz, 1H), 7.24 (d, J = 3.6 Hz, 1H), 6.97 (s, 1H), 6.92 (dd, |

-continued

| Cpd No. | Name | Starting boronate | Starting chloro-pyrimidine | NMR data |
|---|---|---|---|---|
|  | pentyl}-7H-pyrrolo[2,3-d]pyrimidin-4-yl)-6-methoxy-1H-indole-1-carboxylate | 1H-indole-1-carboxylate | pyrrolo[2,3-d]pyrimidin-7-yl)cyclopentyl] methanol | J = 8.6, 2.3 Hz, 1H), 6.60 (d, J = 3.6 Hz, 1H), 5.67 (s, 1H), 5.61-5.46 (m, 1H), 4.61 (s, 1H), 4.47 (t, J = 9.5 Hz, 1H), 4.31 (dd, J = 9.9, 5.9 Hz, 1H), 2.95-2.85 (m, 1H), 2.47-2.16 (m, 3H), 2.10 (td, J = 9.3, 4.7 Hz, 1H) and 1.22 (d, J = 5.0 Hz, 9H). |
| I-14 | [(1S,2S,4R)-2-hydroxy-4-{6-[6-(trifluoromethyl)-1H-indol-2-yl]-7H-pyrrolo[2,3-d]pyrimidin-7-yl}cyclopentyl]methyl sulfamate | 2-(4,4,5,5-tetramethyl-1,3,2-dioxaborolan-2-yl)-6-(trifluoromethyl)-1H-indole | [(1S,2S,4R)-2-{[tert-butyl(dimethyl)silyl]oxy}-4-(4-chloro-7H-pyrrolo[2,3-d]pyrimidin-7-yl)cyclopentyl] methanol | $^1$H NMR (400 MHz, CD$_3$OD) δ 8.82 (s, 1H), 8.18 (s, 1H), 7.84 (d, J = 8.4 Hz, 2H), 7.71 (d, J = 3.7 Hz, 1H), 7.62 (s, 1H), 7.31 (d, J = 8.9 Hz, 1H), 7.12 (d, J = 3.6 Hz, 1H), 5.63 (s, 1H), 4.54 (s, 1H), 4.40 (dd, J = 9.6, 7.6 Hz, 1H), 4.29-4.11 (m, 1H), 2.91 (s, 1H), 2.45-2.22 (m, 3H) and 2.16 (dd, J = 9.2, 5.0 Hz, 1H). |
| I-02 | {(1S,2S,4R)-2-hydroxy-4-[4-(1-methyl-1H-indol-2-yl)-7H-pyrrolo[2,3-d]pyrimidin-7-yl]cyclopentyl}methyl sulfamate HCl | 1-methyl-2-(4,4,5,5-tetramethyl-1,3,2-dioxaborolan-2-yl)-1H-indole | [(1S,2S,4R)-2-{[tert-butyl(dimethyl)silyl]oxy}-4-(4-chloro-7H-pyrrolo[2,3-d]pyrimidin-7-yl)cyclopentyl] methanol | $^1$H NMR (400 MHz, d$_6$-DMSO) δ 8.82 (s, 1H), 7.83 (d, J = 3.7 Hz, 1H), 7.58 (d, J = 7.9 Hz, 1 H), 7.48 (d, J = 8.4 Hz, 1H), 7.30 (s, 2H), 7.23-7.16 (m, 1H), 7.15 (s, 1H), 7.02 (dd, J = 11.0, 3.9 Hz, 1H), 6.83 (d, J = 3.7 Hz, 1H), 5.53-5.38 (m, 1H), 4.26 (3, 1H), 4.14 (dd, J = 9.7, 7.0 Hz, 1H), 4.01-3.89 (m, 4H), 2.67 (d, J = 4.2 Hz, 1H), 2.23-1.98 (m, 3H) and, 1.98-1.84 (m, 1H). |

Example 8d

The following compound was prepared as described in Examples 6-8 using the appropriate boronate and chloropyrimidine:

| Cpd No. | Name | Starting boronate | Starting chloro-pyrimidine | NMR data |
|---|---|---|---|---|
| I-02 | {(1S,2S,4R)-2-hydroxy-4-[4-(1-methyl-1H-indol-2-yl)-7H-pyrrolo[2,3-d]pyrimidin-7-yl]cyclopentyl}methyl sulfamate HCl | 1-methyl-2-(4,4,5,5-tetramethyl-1,3,2-dioxaborolan-2-yl)-1H-indole | [(1S,2S,4R)-2-{[tert-butyl(dimethyl)silyl]oxy}-4-(4-chloro-7H-pyrrolo[2,3-d]pyrimidin-7-yl)cyclopentyl]methanol | $^1$H NMR (400 MHz, d$_6$-DMSO) δ 8.82 (s, 1H), 7.83 (d, J = 3.7 Hz, 1H), 7.58 (d, J = 7.9 Hz, 1H), 7.48 (d, J = 8.4 Hz, 1H), 7.30 (s, 2H), 7.23-7.16 (m, 1H), 7.15 (s, 1H), 7.02 (dd, J = 11.0, 3.9 Hz, 1H), 6.83 (d, J = 3.7 Hz, 1H), 5.53-5.38 (m, 1H), 4.26 (s, 1H), 4.14 (dd, J = 9.7, 7.0 Hz, 1H), 4.01-3.89 (m, 4H), 2.67 (d, J = 4.2 Hz, 1H), 2.23-1.98 (m, 3H) and, 1.98-1.84 (m, 1H). |

Biological Assays

UBA6 AlphaScreen® Assay.

The UBA6 enzmatic reaction totals 20 μL and contains 50 mM HEPES (pH 7.5), 0.05% BSA, 0.02% Tween 20, 0.1 mM TCEP, 5 mM MgCl2, 2 μM ATP, 60 nM Flag-Ubiquitin, 20 nM Biotin-his-Use1, and 0.15 nM recombinant human his-UBA6 enzyme. The enzymatic reaction mixture, with and without compound inhibitor, is incubated at 24° C. for 90 minutes in a 384 well plate before termination with 10 μL of Stop/Detection buffer (50 mM HEPES (pH 7.5), 0.05% BSA, 0.02% Tween 20, 0.1 mM TCEP, 20 mM EDTA, 30 μg/ml anti-FLAG Acceptor beads (Perkin Elmer), and 6 μg/mL streptavidin donor beads (Perkin Elmer). After incubation for 2 hours at 24° C. in a dark room, quantification of the AlphaScreen signal is performed on the Pherastar™ (BMG).

| Compound no. | Example no. | % inhibition @0.123 μM | IC$_{50}$[†] |
|---|---|---|---|
| I-01 | 8 | 87 | A |
| I-02 | 8b | 5.9 | B |
| I-03 | 6a | 93 | A |
| I-04 | 6c | 91 | A |
| I-05 | 6c | 86 | A |
| I-06 | 8a | 88 | A |
| I-07 | 8a | 90 | A |
| I-08 | 8a | 74 | A |
| I-09 | 8a | 49 | B |

-continued

| Compound no. | Example no. | % inhibition @0.123 μM | IC$_{50}$† |
|---|---|---|---|
| I-10 | 8b | 26‡ | B |
| I-11 | 6b | 61 | B |
| I-12 | 6b | 12 | B |
| I-13 | 6b | 16 | B |
| I-14 | 8b | 32 | B |

†A means IC$_{50}$ ≤ 50 nM
B means 50 nM < IC$_{50}$ ≤ 2.0 μM
‡This value was obtained @ 1.11 μM Cell Based Assay.

Compound cell activity is judged by analysis of appropriate marker proteins by standard western blot. WSU-DLCL2 cells are grown overnight in RPMI1640 medium supplemented with 10% fetal bovine serum and then seeded in six-well culture dishes at a density of 2×10e6 cells/mL. Compound is added at 10 μM and the cells are further cultured for 6 hours whereupon cells are harvested by centrifugation and washed one time with ice-cold PBS. Cells are lysed in buffer (150 mM NaCl, 1% NP-40, 50 mM MES pH 4.5) supplemented with standard protease and phosphatase inhibitors and iodoacetimide. Lysates are clarified by centrifugation in a tabletop centrifuge at 4° C. Equal amounts of protein based on cell equivalents are resolved by SDS-PAGE and transblotted to nitrocellulose. An antibody to SQLE was purchased from Abcam (Cat#ab67479). Impact on SREBP-dependent lipid metabolism was assessed by loss of squalene epoxidase (SQLE) J. Horton, et al., *PNAS*, 2002, 100(21), 12027-32 and is shown in FIG. 1 for compound I-01, I-02, and I-08.

While a number of embodiments of this invention have been described, it is apparent that the provided examples may be altered to convey other embodiments, which utilize the chemical entities and methods of this invention. It will thus be appreciated that the scope of this invention has been represented herein by way of example and is not intended to be limited by the specific embodiments described.

What is claimed is:

1. A chemical entity which is a compound of Formula I:

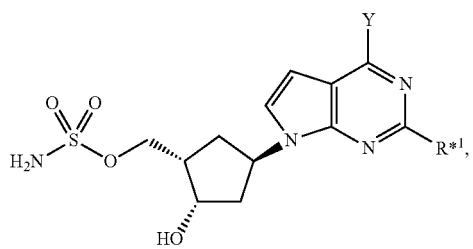

or a pharmaceutically acceptable salt thereof, wherein:
$R^{*1}$ is —H or —CH$_3$;
Y is

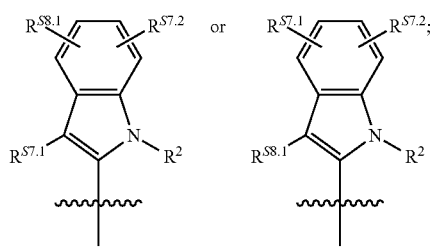

$R^2$ is —H, —CH$_3$ or —C(=O)—OR$^{†4}$;
each of $R^{S7.1}$ and $R^{S7.2}$ is independently —H, (a) halo, (b1) C$_{1-3}$ aliphatic, (b2) R$^{\#2-1}$, (c) —OR$^{*3}$, (d) —N(R$^{*3}$)$_2$ or (e) —SR$^{†3}$;
$R^{S8.1}$ is —H, (a) halo, (b1) C$_{1-4}$ aliphatic, (b2) R$^{\char`\~4-2}$, (c) —OR$^{*4}$, (d) —N(R$^{*4}$)$_2$, (e) —SR$^{†4}$, (f) C$_{1-3}$ fluoroalkyl, (g1) C$_{1-2}$ fluoroalkoxy, (g2) C$_{1-2}$ fluoroalkylthio, (h) —NO$_2$, (i) —CN, (j) —C(O)—R$^{†4}$, (k) —C(O)—OR$^{*4}$, (l) —C(O)—N(R$^{*4}$)$_2$, (n) —N(R$^{*4}$)—C(O)—R$^{†4}$, (q) —N(R$^{*4}$)—C(O)—OR$^{*4}$ or (r) —N(R$^{*4}$)—C(O)—N(R$^{*4}$)$_2$;
provided that at least one of $R^{S7.1}$, $R^{S7.2}$ and $R^{S8.1}$ is —H;
each instance of $R^{*4}$ is independently —H or C$_{1-4}$ alkyl;
each instance of $R^{*3}$ is independently —H or C$_{1-3}$ alkyl;
each instance of $R^{†4}$ is independently C$_{1-4}$ alkyl;
each instance of $R^{†3}$ is independently C$_{1-3}$ alkyl;
each instance of R$^{\char`\~4-2}$ is independently

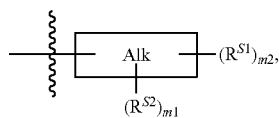

wherein

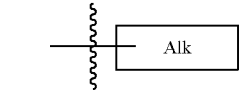

represents C$_{1-4}$ alkyl; and
each of m1 and m2 is independently 0 or 1;
each instance of $R^{\#2-1}$ is independently

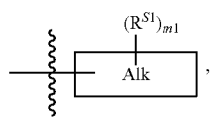

wherein

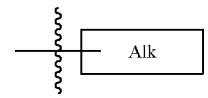

represents C$_{1-2}$ alkyl; and
m1 is 0 or 1;
each instance of $R^{S1}$ is independently —H, (a) halo, (c) —OR$^{*2}$, (d) —N(R$^{*2}$)$_2$ or (e) —SR$^{†2}$; and
each instance of $R^{S2}$ is independently —H, (a) halo, (c) —OR$^{*2}$, (d) —N(R$^{*2}$)$_2$, (e) —SR$^{†2}$, (h) —NO$_2$, (i) —CN, (j) —C(O)—R$^{†2}$, (k) —C(O)—OR$^{*2}$, (l) —C(O)—N(R$^{*2}$)$_2$, (m) —O—C(O)—R$^{†2}$, (n) —N(R$^{*2}$)—C(O)—R$^{†2}$, (o) —O—C(O)—OR$^{*2}$, (p) —O—C(O)—N(R$^{*2}$)$_2$, (q) —N(R$^{*2}$)—C(O)—OR$^{*2}$ or (r) —N(R$^{*2}$)—C(O)—N(R$^{*2}$)$_2$;
each instance of $R^{*2}$ is independently —H or C$_{1-2}$ alkyl; and
each instance of $R^{†2}$ is independently C$_{1-2}$ alkyl.

2. The chemical entity of claim 1, wherein
$R^{S8.1}$ is —H, (a) halo, (b1) C$_{1-4}$ aliphatic, (b2) R$^{\#4-2}$, (f) C$_{1-3}$ fluoroalkyl, (h) —NO$_2$, (i) —CN, (j) —C(O)—R$^{†4}$, (k) —C(O)—OR$^{*4}$ or (l) —C(O)—N(R$^{*4}$)$_2$; and each instance of $R^{\#4\text{-}2}$ is independently

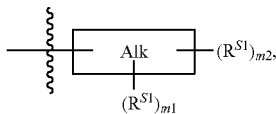

wherein

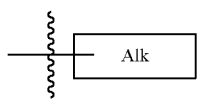

represents $C_{1\text{-}4}$ alkyl; and
each of m1 and m2 is independently 0 or 1.

3. The chemical entity of claim 1, wherein
each of $R^{S7.1}$ and $R^{S7.2}$ is independently —H, (a) halo, (b1) $C_{1\text{-}3}$ aliphatic or (c) —OR*³; and
$R^{S8.1}$ is —H, (f) $C_{1\text{-}3}$ fluoroalkyl or (i) —CN.

4. The chemical entity of claim 1, wherein
each of $R^{S7.1}$ and $R^{S7.2}$ is independently —H, (a) —F, or Cl, (b1) —CH₃ or (c) —OCH₃; and
$R^{S8.1}$ is —H, (f) —CF₃ or (i) —CN.

5. The chemical entity of claim 1, wherein Y is

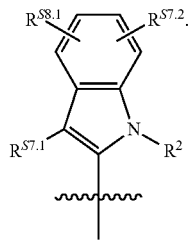

6. The chemical entity of claim 1, wherein $R^2$ is —H.
7. The chemical entity of claim 1, wherein $R^2$ is —C(=O)—O†Bu.
8. The chemical entity of claim 1, wherein $R^{*1}$ is —H.
9. The chemical entity of claim 1, wherein $R^{*1}$ is —CH₃.
10. The chemical entity of claim 1, wherein at least two of $R^{S7.1}$, $R^{S7.2}$ and $R^{S8.1}$ are —H.

11. The chemical entity of claim 1, wherein the compound is
I-01 ((1 S,2S,4R)-4-(4-(1H-indol-2-yl)-7H-pyrrolo[2,3-d]pyrimidin-7-yl)-2-hydroxycyclopentyl)methyl sulfamate HCl;
I-02 {(1S,2S,4R)-2-hydroxy-4-[4-(1-methyl-1H-indol-2-yl)-7H-pyrrolo[2,3-d]pyrimidin-7-yl]cyclopentyl}methyl sulfamate HCl;
I-03 {(1S,2S,4R)-2-hydroxy-4-[4-(5-methoxy-1H-indol-2-yl)-7H-pyrrolo[2,3-d]pyrimidin-7-yl]cyclopentyl}methyl sulfamate;
I-04 {(1S,2S,4R)-4-[4-(6-chloro-1H-indol-2-yl)-7H-pyrrolo[2,3-d]pyrimidin-7-yl]-2-hydroxycyclopentyl}methyl sulfamate;
I-05 {(1S,2S,4R)-4-[4-(6-cyano-1H-indol-2-yl)-7H-pyrrolo[2,3-d]pyrimidin-7-yl]-2-hydroxycyclopentyl}methyl sulfamate;
I-06 {(1S,2S,4R)-2-hydroxy-4-[4-(6-methyl-1H-indol-2-yl)-7H-pyrrolo[2,3-d]pyrimidin-7-yl]cyclopentyl}methyl sulfamate;
I-07 {(1 S,2S,4R)-2-hydroxy-4-[4-(6-methoxy-1H-indol-2-yl)-7H-pyrrolo[2,3-d]pyrimidin-7-yl]cyclopentyl}methyl sulfamate;
I-08 {(1S,2S,4R)-2-hydroxy-4-[4-(1H-indol-2-yl)-2-methyl-7H-pyrrolo[2,3-d]pyrimidin-7-yl]cyclopentyl}methyl sulfamate HCl;
I-09 {(1 S,2S,4R)-4-[4-(6-chloro-5-fluoro-1H-indol-2-yl)-7H-pyrrolo[2,3-d]pyrimidin-7-yl]-2-hydroxycyclopentyl}methyl sulfamate;
I-10 tert-butyl 2-(7-{(1R,3S,4S)-3-hydroxy-4-[(sulfamoyloxy)methyl]cyclopentyl}-7H-pyrrolo[2,3-d]pyrimidin-4-yl)-6-methoxy-1H-indole-1-carboxylate;
I-11 {(1S,2S,4R)-4-[4-(5-fluoro-1H-indol-2-yl)-7H-pyrrolo[2,3-d]pyrimidin-7-yl]-2-hydroxycyclopentyl}methyl sulfamate;
I-12 {(1 S,2S,4R)-2-hydroxy-4-[4-(7-methoxy-1H-indol-2-yl)-7H-pyrrolo[2,3-d]pyrimidin-7-yl]cyclopentyl}methyl sulfamate;
I-13 {(1S,2S,4R)-2-hydroxy-4-[4-(3-methyl-1H-indol-2-yl)-7H-pyrrolo[2,3-d]pyrimidin-7-yl]cyclopentyl}methyl sulfamate; or
I-14 [(1S,2S,4R)-2-hydroxy-4-{4-[6-(trifluoromethyl)-1H-indol-2-yl]-7H-pyrrolo[2,3-d]pyrimidin-7-yl}cyclopentyl]methyl sulfamate.

12. A composition comprising, the chemical entity of claim 1, and a pharmaceutically acceptable carrier.

* * * * *